United States Patent [19]
Cathcart et al.

[11] Patent Number: 5,346,999
[45] Date of Patent: Sep. 13, 1994

[54] METHOD OF NUCLEIC ACID EXTRACTION

[75] Inventors: Guy R. Cathcart, Berkeley; Paul D. Grossman, Foster City; P. Eric Mayrand, Pacifica; Eric S. Nordman, San Bruno; Norman M. Whiteley, San Carlos, all of Calif.

[73] Assignee: Applied Biosystems, Inc., Foster City, Calif.

[21] Appl. No.: 328,471

[22] Filed: Mar. 24, 1989

Related U.S. Application Data

[63] Continuation-in-part of Ser. No. 692,958, Jan. 18, 1985, abandoned, and a continuation-in-part of Ser. No. 850,869, Apr. 11, 1986, abandoned.

[51] Int. Cl.$^5$ .............................................. C07H 23/00
[52] U.S. Cl. .................... 536/25.41; 536/26.73; 536/26.12; 436/175; 436/177
[58] Field of Search ............... 435/315, 285, 287, 290; 204/234; 210/22; 422/10; 536/27, 25.41, 26.73, 27.12; 436/177, 175; 935/19, 20, 21

[56] References Cited

U.S. PATENT DOCUMENTS

| | | | |
|---|---|---|---|
| 2,967,093 | 1/1961 | Raymond | 422/101 |
| 3,389,133 | 6/1968 | Gutcho | 260/211.5 |
| 3,617,547 | 11/1971 | Halff et al. | 210/22 |
| 3,847,749 | 11/1974 | Smith et al. | 435/285 |
| 3,926,738 | 12/1975 | Nyiri et al. | 435/290 |
| 3,935,092 | 1/1976 | Bizot et al. | 204/234 |
| 4,264,741 | 4/1981 | Friedman et al. | 435/312 |
| 4,460,575 | 7/1984 | d'Hinterland et al. | 424/92 |
| 4,598,049 | 7/1986 | Zelinka et al. | 435/289 |
| 4,985,352 | 1/1991 | Julius et al. | 435/6 |
| 5,122,599 | 6/1992 | Barnett et al. | 536/27 |

FOREIGN PATENT DOCUMENTS 2625208 12/1977 Fed. Rep. of Germany .

OTHER PUBLICATIONS

Favloro et al. "Transcription Maps . . . Gel Mapping", Methods in Enzymology, 65, 718–723.
Nevins "Definition and Mapping . . . Transcription", Methods in Enzymology, 65, 768–775.
Hewlett-Packard Co. v. Bausch & Lomb Inc., 15USPQ2d. 1525. decided Jul. 30, 1990.
Adamson, Physical Chemistry of Surfaces, 4th Ed. pp. 471–474 Wiley–Interscience, 1982.
Maniatas et al.: Molecular Cloning, A Laboratory Manual, 1982, pp. 280, 366, 458–459, Cold Spring Harbor.
Weber:Physicochemical Process for Water Quality Control, Wiley–Interscience, 1972, p. 92.
Fujimoto, New Introduction to Surface Active Agents (Sanyo Chemical Industries, Ltd., Kyoto, 1985).
Coombs, Dictionary of Biotechnology (Elsevier, New York).
Wait et al., Applied and Environmental Microbiology, 46: 379–385 (1983).
Grossman and Moldave, eds., pp. 112–160 in Methods in Enzymology, vol. XII (Academic Press, New York, 1968).
Kirby, pp. 1–5 in Progress in Nucleic Acid Research and Molecular Biology, vol. 3 (Academic Press, New York, 1964).
Marmur, J. Mol. Biol., 3: 208–218 (1961).
Marmur, Methods in Enzymology, vol. VI, pp. 726–738 (1963).
Kirby, Biochem. J. 66: 495–503 (1957).

Primary Examiner—James C. Housel
Assistant Examiner—N. Bhat
Attorney, Agent, or Firm—Joseph H. Smith; Ronald E. Grubman

[57] ABSTRACT

An automated apparatus is provided which implements a new method of extracting and purifying nucleic acids from cells without the use of centrifugation. In the method, a lysate is created by treating the cells with proteinase K in the presence of a lysis buffer having a high concentration of a salt. The lysate is mixed with a phenol-based solvent system, thereby creating an emulsion. The emulsion is heated to promote phase separation. Similarly, the rate of phase separation is also enhanced by increasing the surface area of the emulsion. Once the phase separation is complete, the lower organic phase is removed and the upper aqueous phase is repeatedly extracted with the phenol-based solvent a preselected number of times, and is finally extracted using chloroform. The remaining aqueous phase is then dialyzed to further purify and concentrate the nucleic acid solution. Two preferred embodiments of apparatus are presented to accomplish this extraction.

19 Claims, 15 Drawing Sheets

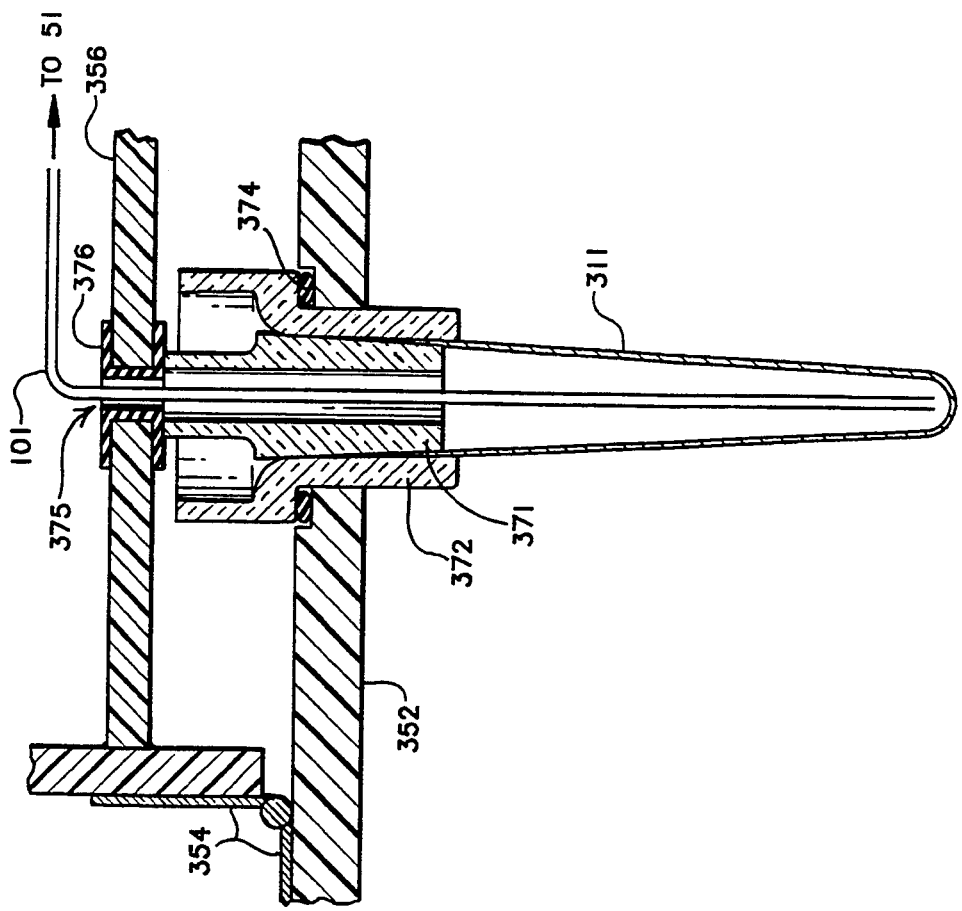
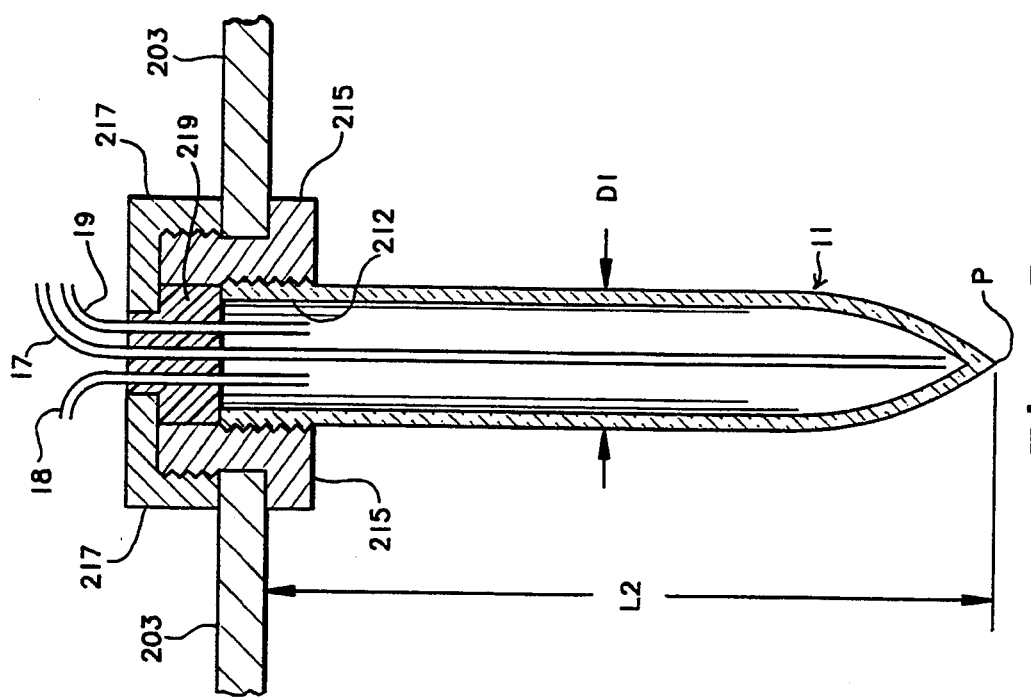
Fig. 6
Fig. 5

METHOD OF NUCLEIC ACID EXTRACTION

This is a continuation-in part of copending application Ser. No. 692,958, filed Jan. 18, 1985 and a continuation-in-part of copending application Ser. No. 850,869 filed Apr. 11, 1986.

BACKGROUND OF THE INVENTION

This invention relates to the isolation and purification of nucleic acids from cells, and particularly to apparatus for automatically achieving such isolation.

One of the first steps in the in vitro manipulation of nucleic acids involves their isolation. For example, relatively pure samples of genomic DNA are required in order to perform tests for genetic desease and recombinant technology requires isolation of both the vector DNA and the DNA to be cloned.

As a general rule, DNA does not exist as a free molecule in a cell, but instead exists as a complex association of DNA, RNA and proteins. This is a consequence of the role of DNA as the genetic information, the DNA is used as a template for the production of messenger RNA, which is translated by the ribosome into protein. Proteins directly involved in the process of gene expression, such as RNA polymerase and regulatory proteins, interact with DNA in vivo to form nucleo-protein complexes, DNA polymerase, DNA ligase, various unwinding and supercoiling enzymes, recombination and repair enzymes, and those proteins involved in the initiation or maintenance of DNA replication are also associated with DNA in vivo and hence complicate the isolation of pure DNA. Because of this complex association of DNA with these other proteins and nucleic acids, the purification (isolation) approach for obtaining DNA can generally be thought of as a three step process: (1) releasing soluble, high molecular weight DNA from disrupted cell wall and membranes; (2) dissociating DNA-protein complexes by protein denaturation or proteolysis; and (3) separating DNA from the other macromolecules.

Within this process, DNA of bacterial origin (prokaryotic DNA) is typically purified by different methods, depending on whether the DNA is chromosomal DNA, the bacterial cell wall is generally weakened by freeze-thawing or by treatment with the enzyme lysozyme and the chelating agent ethylenediaminetetraacetic acid (EDTA). Cell lysis is accomplished by the addition of a detergent such as sodium dodecyl sulfate (SDS) in a buffered saline solution. Following lysis, the solution is treated with pancreatic ribonuclease to hydrolyze RNA and protease to degrade proteins. Residual proteins and oligopeptides are extracted with an organic solvent, such as phenol or an equal mixture of phenol and chloroform. Most of the protein will denature and enter the organic phase or precipitate at the interface of the organic and aqueous phases, this phase separation being accomplished by means of centrifugation. The clear, viscous aqueous phase containing the DNA is then removed. With the addition of alcohol, the DNA precipitates out of the aqueous phase as a white fibrous material and can be spooled onto a glass rod. Precipitation from alcohol serves to concentrate the high molecular weight DNA while removing the small oligonucleotides of DNA and RNA, detergent, and the organic solvent used in the removal of proteins. Residual detergent and salts can be removed by dialysis of the resuspended DNA solution against the desired buffer. In some instances, it may be desirable to further purify the DNA by centrifugation on isopycnic cesium chloride gradients, or by hydroxylapatite chromatography. In the above process for chromosomal DNA, typical protocols often require at least two days for the DNA extraction and purification process. (See *Recombinant Techniques* by Raymond L. Rodrigues, and Robert C. TAct, 1983, p. 162).

During the purification of extrachromosomal elements of prokaryotic DNA, including plasmids and bacteriophage, it is desirable to minimize the amount of chromosomal DNA contaminating the preparation. With Bacteriophage, this is often accomplished by first purifying the phage particles from the infected bacteria, then treating the purified phage particles with protease and/or phenol to release the bacteriophage DNA. Further purification of the DNA is accomplished by means similar to those described for chromosomal DNA. Due to its size, however, precipitated bacteriophage and plasmid DNA cannot be spooled out on a glass rod and is therefore generally recovered by centrifugation. Again, three days is not atypical for the entire isolation and purification process.

For eukaryotic cells, isolation and purification of total cellular DNA is often achieved by a modification of the detergent lysis procedure described above for bacteria. The key difference is that typically cell lysis and digestion of cellular proteins are accomplished using proteinase K in the presence of the detergent. (See M. Gross-Bellard, P. Oudet, and P. Chambon, Eur. J. Biochem., 36 (1973) 32–38; N. Blin, and D. W. Stafford, Nuc. Acid. Res., 3 (1976) 2303–2308; and D. J. Law, P. M. Frossard and D. L. Ruchnagel, Gene, 28 (1984) 153–158. The proteinase K is then removed by extraction of the lysate with phenol or a phenol/chloroform mixture. Typically, in the mixing process as for the extraction of bacterial DNA, the lysate/phenol or lysate/phenol-chloroform forms an emulsion, the aqueous and organic phases of which are separated by centrifugation. The upper, or aqueous, phase containing the DNA is then poured off or removed using a pipette, and this essentially protein-free lysate is dialyzed to remove small molecular weight cellular contaminants and residual phenol.

In the above approaches, a major limitation on the extraction which critically limits the ability to automate the process, is the need for centrifugation to separate the aqueous and organic phases during the phenol extraction. Often several extractions are required to achieve the desired purity, each one requiring centrifugation. Largely due to these various centrifugations, the work is performed manually and is therefore expensive. Also these configurations make automating of the extraction process difficult and expensive.

SUMMARY OF THE INVENTION

In accordance with a preferred embodiment of the invention, an automated apparatus is provided which implements a new method of extracting and purifying nucleic acids from cells without the use of centrifugation. In the method, a lysate is created by treating the cells with proteinase K in the presence of a lysis buffer having a high concentration of a salt. The lysate is mixed with a phenol-based solvent system, thereby creating an emulsion. The emulsion is heated to promote phase separation. Similarly, the rate of phase separation is also enhanced by increasing the surface area of the emulsion. Once the phase separation is complete, the lower organic phase is removed and the upper aqueous phase is repeatedly extracted with the phenol-based solvent a preselected number of times, and is finally extracted using chloroform. The remaining aqueous phase is then dialyzed to further purify and concentrate the nucleic acid solution.

The apparatus for implementing this method includes at least one extraction vessel for holding the sample and a delivery system for delivering reagents to the extraction vessel and for removing fluids from the extraction vessel. Fluids are removed from the extraction vessel typically by pressure transfer. A heating system is provided for maintaining the desired temperature of the extraction vessel during the phase separation process, and a motor is used for gently oscillating the extraction vessel to obtain mixing of the fluids contained therein. The motor also rotates the extraction vessel about a horizontal axis to achieve an increase in surface area of the emulsion resulting from treatment of the lysate with the phenol-based solvent system. The combination of the high salt concentration together with heating and increasing the surface area of the emulsion results in phase separation in 2 to 8 minutes, and thus totally eliminates the need for centrifugation.

A computer system is used for controlling the heating system, the motor, and the delivery system, for timing the flow of the reagents into the reaction vessel to control volume, for monitoring the temperature in the reaction vessel, and for monitoring the flow of the organic phase out of the extraction vessel. The computer also serves as the master timer, timing the mixing by the motor and the wait time during phase separation, and operates according to a preselected instruction set based on the above method. In the first preferred embodiment, a pressurized dialysis system is also included in the apparatus and is coupled to the extraction vessel by the delivery system, in order to have a completely automated system. The dialysis system includes a pump for recirculating dialysate from a bath vessel through a spectophotometer and a filter system back into the bath vessel in order to reuse the dialysate and to avoid excessive replenishment.

In the second preferred embodiment, the extraction vessel and dialysis apparatus are operated independently, but the dialysis system is configured to mate with the extraction vessel for easy transfer of material from one to the other. Also, the apparatus of the second preferred embodiment is especially adapted for normal ethanol precipitation of the nucleic acids.

BRIEF DESCRIPTION OF THE DRAWINGS

FIG. 5 illustrates a preferred design for an extraction vessel and its attachment in the apparatus of the first preferred embodiment.

FIG. 6 illustrates the details of a suspension system for dialysis bags in the dialysis system.

DETAILED DESCRIPTION OF THE INVENTION

Definitions

Figure 1:
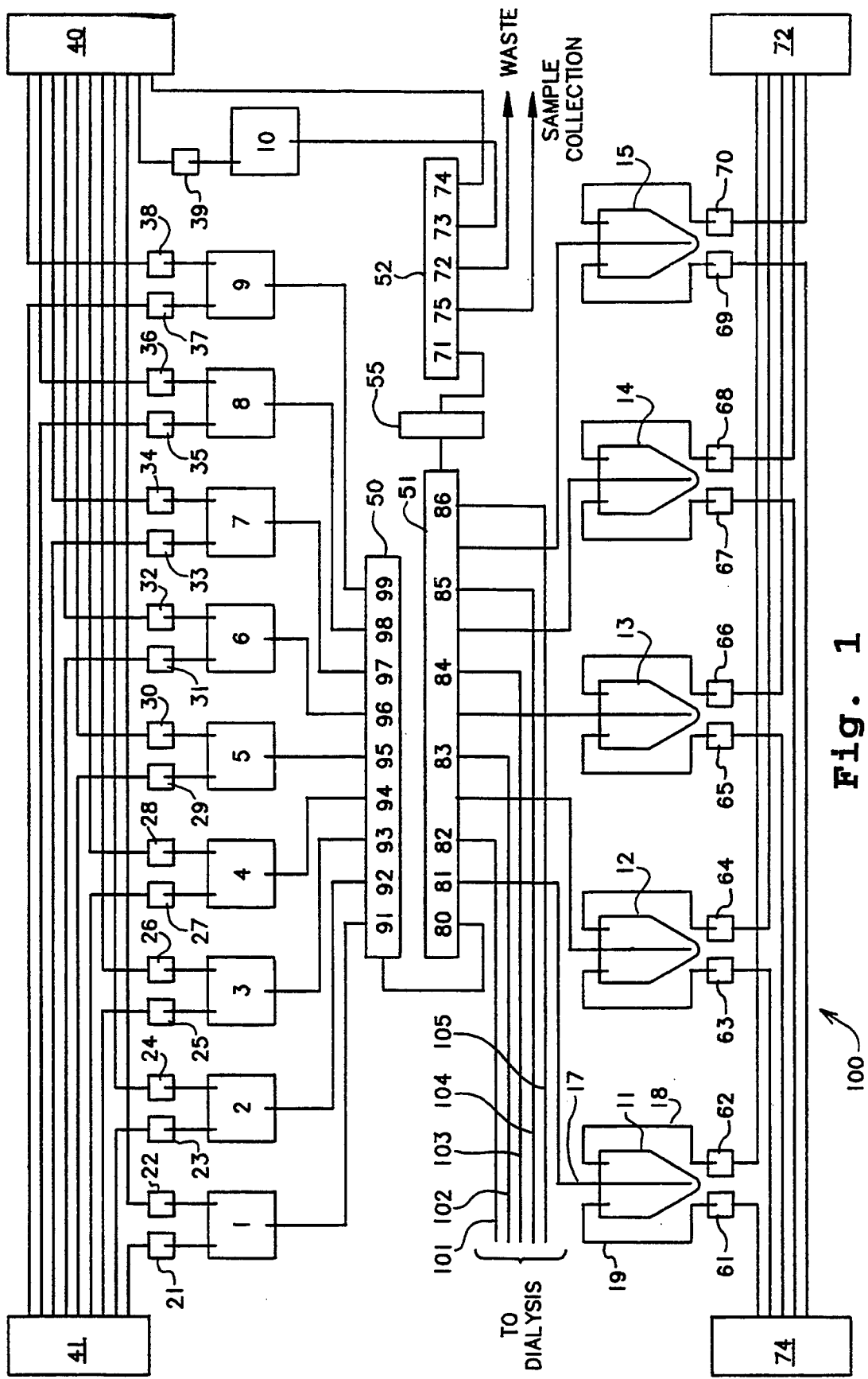
FIG. 1 shows a schematic representation of a fluid delivery system according to the first embodiment of the invention.

For the purpose of the description of the invention, the following definitions will apply:

An "emulsion" is a mixture of two immiscible liquids which are kept in suspension, one within the other. In the context of the extraction of nucleic acids from cells, after cell lysis and mixing of the lysate with a phenol-based solvent system, an emulsion is formed, the constituent fluids of which are an aqueous phase containing the nucleic acids, and an organic phase containing the phenol, denatured proteins, and lipids. In addition to nucleic acids, the aqueous phase also typically contains impurities which in many situations must be removed before further in vitro manipulations can be performed. These impurities include trace amounts of the phenol-based solvent system, many small molecular weight cellular constituents such as carbohydrates, amino acids, and smaller nucleic acids such as nucleosides and nucleotides (usually referred to as the cell sap).

"Dialysis" is a separation process that depends on the differential transport of solutes of different sizes across a porous barrier separating two liquids where the driving force is a concentration gradient only. In the extraction of nucleic acids, dialysis is often used to remove the impurities in the aqueous phase of the emulsion.

"Restriction" is the selective cleaving or endonucleitic cleaving of DNA at unique base sequence sites. Generally, restrictability is considered a strigent test for DNA purity.

Method

The approach of the invention relies on automation of a new method to achieve separation of the organic (phenol) and aqueous (DNA and/or RNA) phases during a nucleic acid extraction without the use of centrifugation. The protocol used is adapted to extraction of nucleic acids from mammalian cells and particularly to high molecular weight DNA (about $10^8$ daltons) from tissues such a peripheral blood lymphocytes, liver, and amniocytes, although it can also be used for other eukaryotic cells if the tissue is properly prepared before the extraction is performed. The protocol in the first embodiment is as follows:

Step 1. The tissue from which the nucleic acid is to be extracted is digested with the enzyme proteinase K in the presence of a lysis buffer. Although it is not required, in the preferred mode, the lysis buffer has a high concentration of a salt to increase ionic strength. The preferred lysis buffer is the mixture 4M urea; 0.5M NaCl; 0.5% SDS, 50 mM Tris-HCl, and 10 mM EDTA, pH 8.0. The digestion is typically performed at about 55° C. for 0.5-3 hours, depending on the nature of cells to be digested. An 8M urea concentration corresponds approximately to saturation and so represents an upper limit. Lower urea concentrations can also be used, and 4M is preferred for best efficiency. A lower limit appears to be about 2M urea. Also, other chaotropic agents, e.g., guanadine hydrochloride, may be substituted for urea. The concentration of the detergent SDS can also be varied, typically from 0.5% to as much as 2%, but a concentration of about 0.5% appears to be more than adequate for most types of mammalian cells. Other detergents such as Triton X-100 TM, Nonedit TM, and lauroyolsarcosine may also be used. Similarly, the high salt concentration can be varied from 0.1M, which considerably slows down phase separation in Step 3 below, to as high as 2M, which does not seem to appreciably increase the rate of phase separation over that obtained with the preferred 0.5M NaCl solution. Other salts, e.g., KCl, may also be used, the preferred concentration depending on the ionic strength of the salt used. Also, chelating agents other than EDTA may be used, for example 8-hydroxyquinoline, and in some instances, the chelating agent may be omitted. The Tris-HCl serves as a buffer.

Step 2. The lysate resulting from Step 1 is gently mixed at room temperature for about 20 minutes with an equal volume of a phenol-based solvent system, preferrably phenol/chloroform/isoamyl alcohol at ratios of about 50:48:2, the phenol for denaturing and extracting the proteins, the chloroform to increase the hydrophobicity, and to ensure that the DNA remains in an aqueous phase (see Step 3), and the isoamyl alcohol to serve primarily as an antisurfactant (antifoaming agent). An emulsion is then formed as a result of the mixing. Variations on this organic solvent system may be used, such as replacing the phenol/chloroform/isoamyl alcohol system with a phenol saturated with Tris-HCl buffer, pH 8.0, or replacing the chloroform with methylene chloride, but the phenol/chloroform/isoamyl alcohol system is preferred because of its efficiency in effecting the desired phase separation in Step 3, and because the DNA does not get lost in the interface between the organic and aqueous phases, as can happen with the system using phenol saturated with buffer. Similarly, the precise volumetric ratios (i.e., 50:48:2) of this preferred phenol based solvent system can be varied, but too low of a concentration of chloroform often permits the DNA to enter the organic phase rather than remain in the aqueous phase. A ratio of phenol to chloroform of about 1:1 seems to provide optimum performance. It should also be appreciated that by changing these ratios, DNA can be driven into the organic phase and separation effected from there as well. Similarly, too low of a concentration of the antisurfactant can result in foaming which can clog the tubes.

Step 3. Phase separation of the emulsion resulting from Step 2 is then accomplished by increasing the surface area of the emulsion while heating to a temperature preferably between 35° C. and 55° C., more preferably between 45° C. and 55° C., and most preferably to about 55° C., that latter temperature being close to the boiling point of chloroform. Increasing the surface area is typically done by positioning the reaction vessel containing the emulsion on its side which increases the cross-sectional area of the interface between the lysate and organic phase and decreases the depth of the two phases. The combination of the high concentration of salt, the large interface area, and the process of heating during this step causes the emulsion to separate into a two-phase system in 2 to 8 minutes, thus totally eliminating the need for centrifugation.

Step 4. The reaction vessel is slowly returned to its normal upright position to maintain the phase separation.

Step 5. The lower phenol phase is educted to waste.

Step 6. The extraction procedure, Steps 2 through 5 above are repeated until the upper phase containing the nucleic acids is free of proteins. Typically only one additional extraction is required for the isolation of nucleic acids from lymphocytes, whereas for some other cell types, for example liver, as many as three additional extractions may be required. Typically, the final extraction is performed with chloroform alone which removes most of the residual phenol, rather than with the phenol/chloroform/isoamyl alcohol mixture.

Step 7. The aqueous phase remaining after Step 6 is educted to a dialysis apparatus, if dialysis is the preferred mode of final DNA purification. As an option, the DNA or RNA can be precipitated out using standard ethanol precipitation, if dialysis is not used to concentrate the sample.

Step 8. The solution removed in Step 7 is dialyzed, typically under pressure, to concentrate the nucleic acids.

Step 9. As an optional step, after Step 8, the aqueous phase can be treated with either RNase or DNase, and the extraction Steps 2 through 8 repeated to leave only DNA or RNA, respectively, in the aqueous phase.

Step 10. Collect the purified sample.

Apparatus

In accordance with a first preferred embodiment of the invention, an apparatus for isolating and purifying nucleic acids from cells is illustrated in FIGS. 1, 2A and 2B, 3, and 4, which show respectively, a fluid delivery system 100 for routing the various reagents and gases throughout the system; a chamber/rocker system 200 for controlling the environment and the physical orientation of extraction vessels during the extraction process; a dialysis system 300; and a computer system 400 for effecting automatic control.

The fluid delivery system 100 illustrated in FIG. 1 includes a series of reagent vessels, 1 through 9, and a series of pairs of electrically operated gas valves 21 through 38, with one pair valves for each reagent vessel. Each gas valve of the series 21 through 38 is connected either to a pressure manifold 40 or to a vent manifold 41, and to a particular reagent vessel in the series 1 through 9, in order to control the pressure in that reagent vessel. Such reagent vessels are typically constructed of glass or polyethylene, depending on the reagent contained therein. For the particular protocol used in the extraction process described above, the reagents include the enzyme proteinase K; the lysis buffer made up of 4M urea, 0.5M NaCl, 0.5% SDS, 50 mM Tris-HCl, and 10 mM EDTA, pH 8.0; the mixture of phenol/chloroform/isoamyl alcohol (50:48:2); chloroform; and RNase and/or DNase. For other protocols, such as for extractions from bacteria and yeasts, other reagents which might be used would include for example, lysozyme, DSD, ethanol, Tris-HCl, EDTA, various saline solutions, and other buffers.

Each of the vessels is coupled to an electrically operated valve block 50, which is an assembly of zero dead volume valves similar to those described in U.S. Pat. No. 4,008,736, issued Feb. 22, 1977, entitled Valve Arrangement For Distributing Fluids, by Wittman-Liebold, et al., as are all other valve blocks in the system. An example of such an electrically operated valve block is manufactured by Applied Biosystems, Inc., part number 600656. Another example is described in copending application "Improved Apparatus and Method for the Sequential Performance of Chemical Processes," filed Nov. 10, 1982, Ser. No. 440,571, k by L. E. Hood, et al., assigned to the same assignee. Fluid flow from the various reagent vessels is controlled by opening the appropriate gas valve and closing the appropriate vent valve to increase the pressure in the desired reagent vessel and opening the appropriate valve in valve block 50. A valve block 51 which is coupled to valve block 50 then directs the flow to a particular extraction vessel, one of vessels 11 through 15. Flow into these extraction vessels is controlled via a series of pairs of electrically operated gas valves 61 through 70, each of which is coupled to either a gas manifold 72 or to a vent manifold 74. Once the extraction in the extraction vessels is complete and organic and aqueous phases have been separated, the organic phase (which is on the bottom in the extraction vessels) is removed by increasing the pressure in the desired extraction vessel, and opening the corresponding valve in valve block 51, thus forcing the fluid out of the vessel through an educting tube, such as tube 17 on extraction vessel 11. Valve block 51 directs the flow through a conductivity detector 55 to another valve block 52 and to waste. A large increase in conductivity is seen when the organic phase has been educted, since the aqueous phase has a high conductivity due to its high salt content. This provides the signal necessary to the computer system to indicate that the phase interface has been detected and to stop any further removal of fluid from the extraction vessel. Once that signal has been received, the waste valve in valve block 52 is closed and either the appropriate dialysis ports of valve block 51, i.e., one or more of ports 82 through 86, are opened to educt the aqueous phase to the dialysis system 300 or the dialysis ports are closed forcing the fluid of the aqueous phase remaining in the fluid delivery lines back into the appropriate reaction vessel in preparation for another phenol/chloroform/isoamyl alcohol extraction. A gas valve 39 is used to force a buffer such as Tris-HCl from an extraction vessel 10 into block valve 52 for backflushing. Those skilled in the art will also understand that in some instances, it may be desired to precipitate out the nucleic acid rather than to concentrate using dialysis. In that instance standard ethanol precipitation can be performed directly in the reaction vessel, or the sample can be educted from the reaction vessel via valve block 51 and can be collected into a separate collection/concentration vessel (not shown) attached to the sample collection line via port 75 of valve block 52.

Tubing such as tube 16 in the above apparatus for connecting the various vessels and valves is typically constructed of Teflon TM. Each tube for transferring liquids in the system has a roughly calibrated flow resistance and operates at a fixed known pressure during transfers due to the pressure manifolds. Hence, the length of time required for a transfer corresponds directly to the volume of material transferred and is controlled by the computer system. Gas flows throughout the system are also controlled by the computer system, the gas valves 21 through 39 and 61 through 70 typically being solenoid operated. An example of such valve includes fluorocarbon valves made by Angar, Inc. An example of an appropriate conductivity detector 55 is a Wescon Instruments Model 219–200 conductivity flow cell coupled to a Model 212–100 conductivity meter.

Figure 2A:
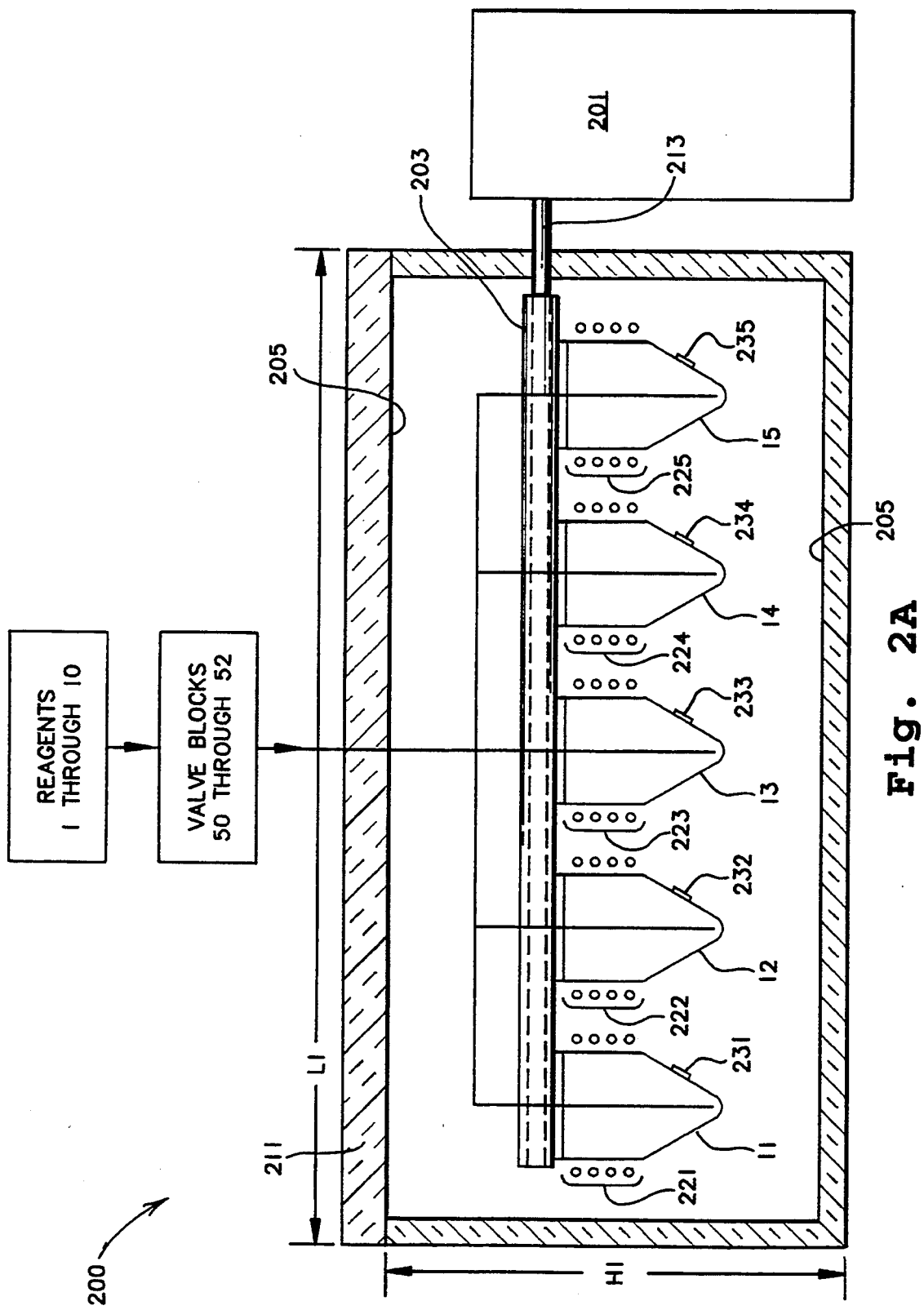
FIGS. 2A and 2B shows two views of a chamber/rocker system according to the first embodiment of the invention.
Figure 2B:
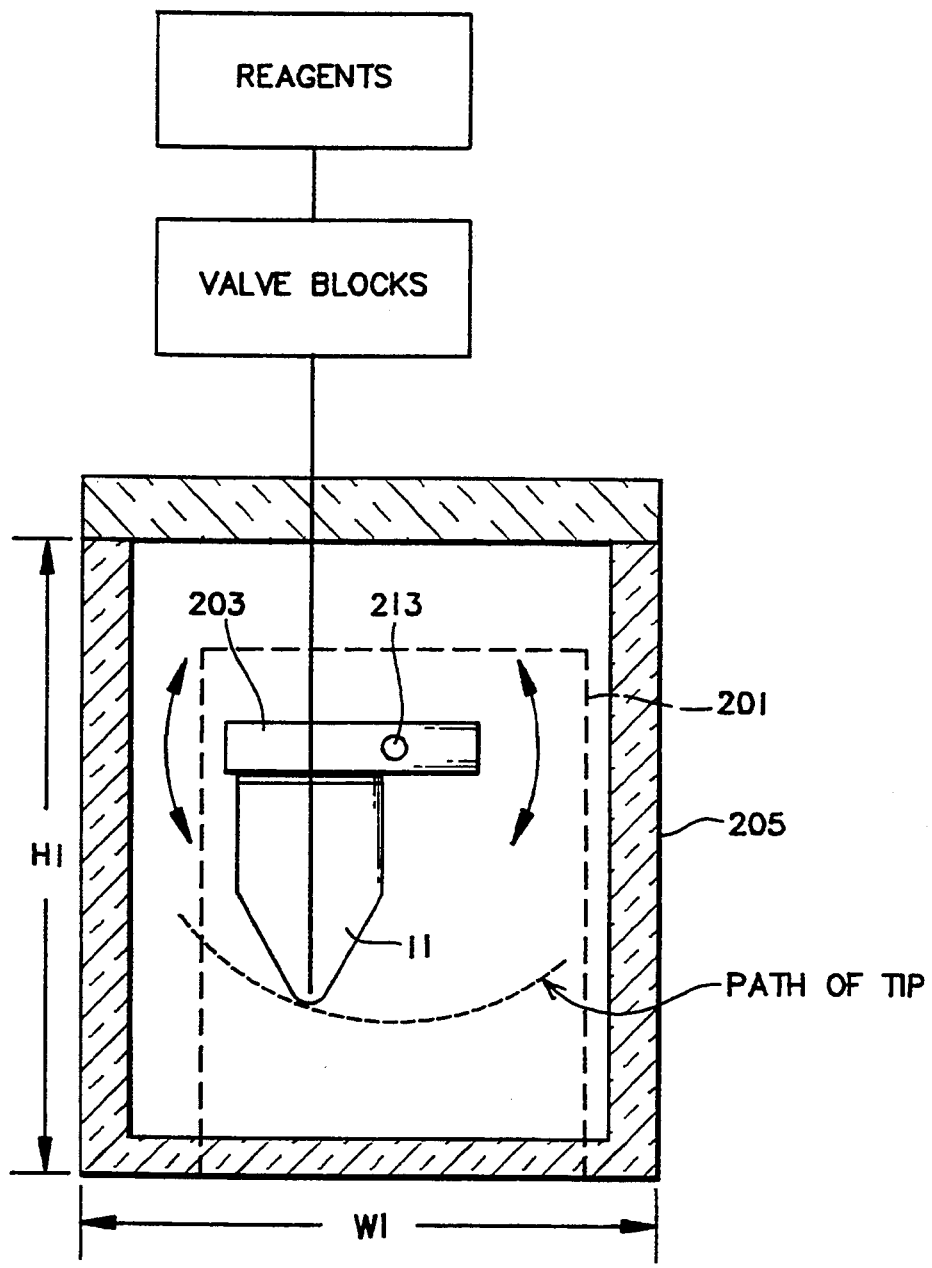

Shown in FIGS. 2A and 2B is the chamber/rocker system 200 which includes a motor 201, a rocker arm 203, and an insulated chamber 205 containing band heaters 221 through 225 (one for each extraction vessel), and corresponding thermisters 231 through 235, and the extraction vessels 11 through 15. In a typical implementation, chamber 205 is a rectangular parallelopiped, generally constructed of plexiglas for ease of construction and because it is transparent, the parallelopiped having a length L1 of about 20", a height H1 of about 14", and a width W1 of about 12", and having an insulating layer 211 located on the top of the parallelopiped to assist in temperature control. Also, one or more fans (not shown) are generally used to maintain ventilation through chamber 205 for cooling the extraction vessels. A typical material for layer 211 is styrofoam about $\frac{1}{2}$" thick. The above dimensions for chamber 205 can vary considerably depending on the desired number and size of extraction vessels, and on the amount of space desired within the chamber to facilitate manipulations of the extraction vessels. Rocker arm 203 is typically a flat sheet of insulating material such plexiglas about $\frac{1}{4}$" to $\frac{1}{2}$" thick, about 16" long, and about 4" wide. Attached firmly to the rocker arm 203, generally along the length of the rocker arm, is a rocker arm shaft 213, typically metal, which is essentially an extended drive shaft for motor 201. Rocker arm 203 typically has holes bored therethrough to accommodate threaded fittings for holding each of the extraction vessels firmly in place, the extraction vessels typically having a threaded top and the fitting having three holes therethrough to accommodate the teflon lines for gas and liquid flow into the vessels. In the preferred mode, motor 201 is a stepper motor, geared to provide a slow oscillation of approximately one per second of the extraction vessels during mixing operations to avoid shearing of the DNA, that oscillation typically being through an angle of 50° to 60°. During phase separation, the motor 201 is advanced to a position corresponding to full horizontal for the extraction vessels and held for several minutes, and is then returned to normal position (i.e., upright for the extraction vessels), generally over a period of about 10 seconds to ensure that phase separation is maintained. An example of such a motor 201 is an AIRPAX Model K82821-P2 geared down from 0.6 pitch diameter to 3.6.

FIG. 5 illustrates a preferred design for the extraction vessels 11 through 15. Each vessel is constructed of glass and has a total length L2 of about 150 mm, a maximum outside cross-sectional diameter D1 of about 28 mm, and tapers to a point P to facilitate the removal of fluids. In the preferred mode, the vessel is graduated and below a screw top 212 has a volume of about 40 ml. An example of such a vessel is a pyrex conical screw cap centrifuge graduated tube available as Corning stock number 8082. The fittings used to hold the vessels in place in the rocker arm 203 are typically constructed of three pieces: a threaded cap 217; a flanged coupling 215 having a inner threaded opening to accept screw top 212, and an outer threaded area to accept cap 217; and a teflon insert 219 which is press fit into flanged coupling 215 and serves as an inert stopper for the extraction vessel. Insert 219 generally has three holes therethrough to accommodate the required liquids and gases. For example, for extraction vessel 11, there is educting tube 17, a pressure tube 18 which is coupled to gas manifold 72, and a vent tube 19 coupled to vent manifold 74. A key feature of this reaction vessel is the large change in surface area of the fluid it contains which occurs when the tube is reoriented from the vertical position to a horizontal position, this change in surface area enhancing the rate of phase separation of the emulsion. Other vessel shapes can also be used which can attain this change in surface area, and in the general case, the angle of rotation required to increase the surface area of the fluid contained therein may not be a full 90°.

Figure 3:
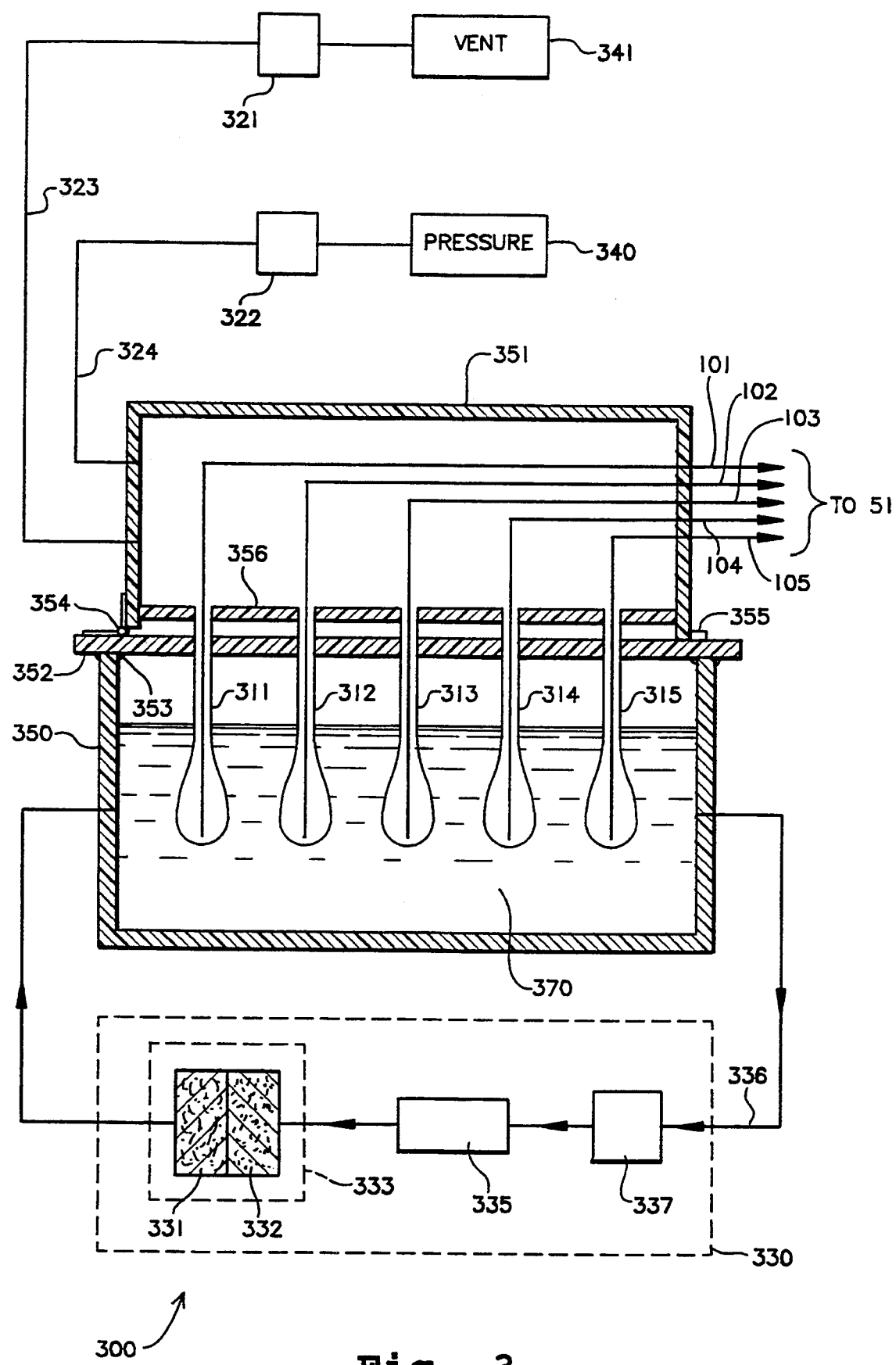
FIG. 3 shows a pressurized dialysis system according to the first embodiment of the invention.

Shown in FIG. 3 is a schematic representation of the pressurized dialysis system 300 which is used for further purifying and concentrating the nucleic acids removed from the extraction vessels 11 through 15. System 300 includes a manifold housing 351 and a bath vessel 350, both of which are typically rectangular in cross-section, the bath vessel generally containing about 8 liters of a dialysate 370. The bath vessel 350 and the manifold housing 351 both abut a cover 352 which is used to exclude foreign matter from the dialysate, with vessel 350 sealed thereto via a seal 353, and manifold housing 351 connected thereto at one side by a hinge 354 and by a clasp 355 at the other side. Bath vessel 350 is generally vented to the ambient atmosphere. In the preferred mode, the bath vessel, the manifold housing and the cover are constructed of plexiglas. Attached to the cover and suspended through holes therein into the dialysate are a plurality of dialysis bags 311 through 315 which are typically in a corresponding relationship with extraction vessels 11 through 15, coupled thereto via valve block 51. Manifold housing 351 includes a bottom piece 356 so that housing 351 is a closed container except for holes through bottom piece 356 to accommodate the dialysis bags, the holes for gas tubes 323 and 324 and for fluid lines 101 through 105; being sealed by feedthroughs. FIG. 6 illustrates the details of the suspension of the dialysis bags and the sealing system so that pressure can be maintained in manifold housing 351 during dialysis. Generally, the dialysis bags are first attached to a glass fitting independent of the dialysis apparatus. For example, dialysis bag 311 is placed over a portion of a short piece of glass tubing 371 and the dialysis bag 311 are pushed firmly into a mated piece of ground glass tubing 372 and given a turn to effect a seal between the two pieces of tubing thereby holding the dialysis bag firmly between them.

The cover 352 is typically drilled to accommodate the larger tubing 372 and the dialysis bag 311 and is counter sunk to accommodate an o-ring seal 374. The dialysis bag and the glass fitting made up of tubing 371 and 372 is then placed through the hole. Bottom piece 356 has a hole 375 which is aligned with the glass fitting when the manifold housing is rotated to the closed position about hinge 354. A grommet seal 376 is located in hole 375 and is used to affect a seal between the glass fitting and the manifold.

The dialysis system 300 also includes a recirculation system 330 having a recirculation tube 336 for extracting dialysate 370 from the bath vessel, a peristaltic pump 337 for pumping the dialysate through the recirculation system, a spectrophotometer 335 for monitoring the absorbance of the dialysate, and a dual in-line filter 333 for filtering out phenol and other organic materials. In a typical implementation, filter 333 includes a carbonaceous filter 332 for removing organic materials, and a mixed bed ion-exchange resin filter 331 for removing organic material. Also, spectrophotometer 335 typically measures absorbance at 270 nm to provide a measure of the phenol remaining in the dialysate. The system generally sets a flag when the absorbance (A270) drops to 0.01 or below, indicating to the computer system that the dialysis function is complete. During dialysis operations, pressure in manifold housing 351 is maintained using an inert gas such as nitrogen and is generally maintained at about 1200 mm Hg (guage) when using dialysis bags such as collodion bags from Schleicher and Schuell having a volume of 2 to 8 ml. Pump 337 typically provides a head of 15 psi and a flow rate of about 1 l/min. Double distilled water is typically used as dialysate 370. The purpose of this recirculation system is to allow the dialysate to be reused instead of being replenished at regular intervals thereby further facilitating automatic operation.

Figure 4:
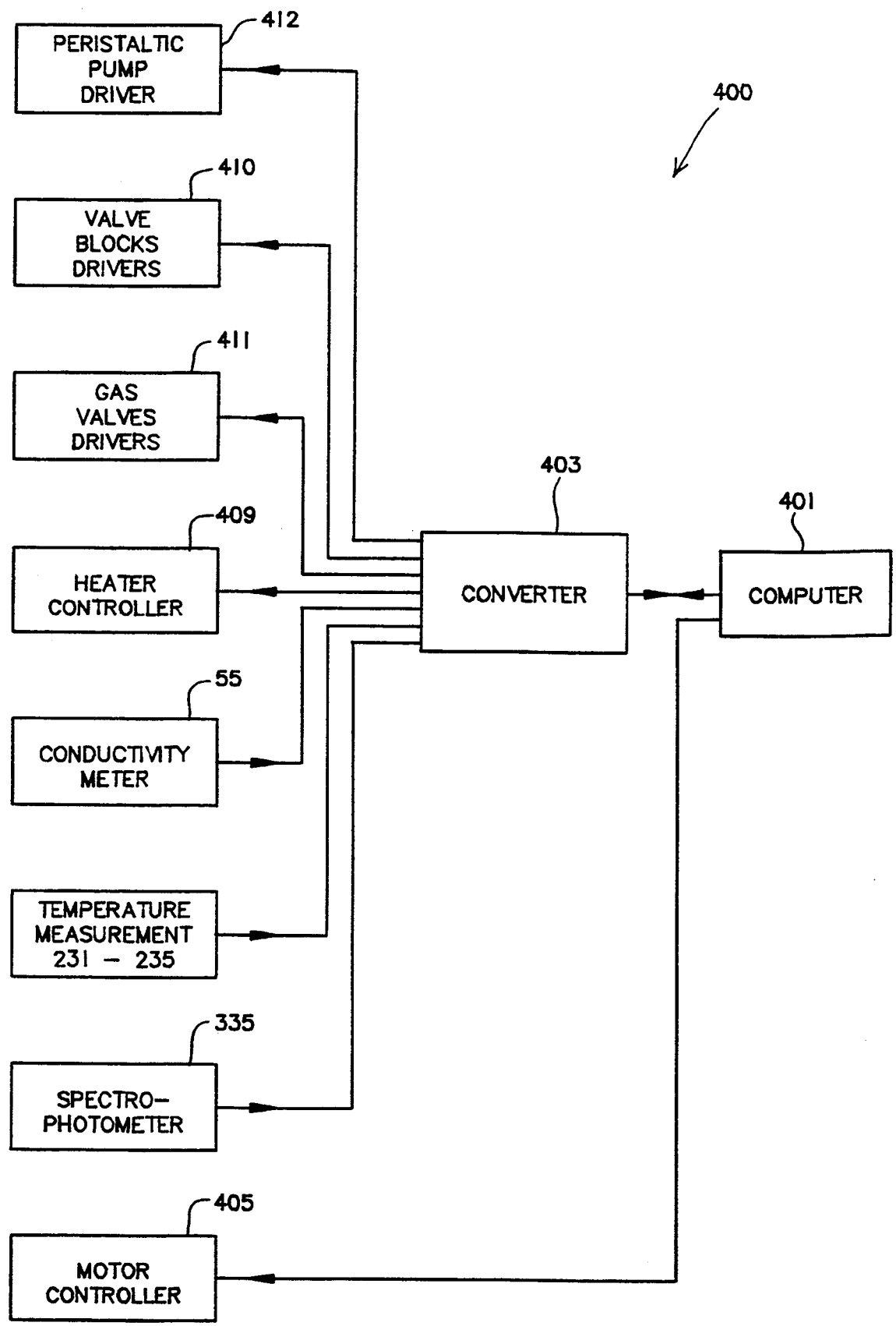
FIG. 4 shows a schematic representation of a computer system according to the invention.

FIG. 4 shows a schematic representation of the computer system 400 used for automatic control. The system is made up of a microprocessor based computer 401 such as a Hewlett-Packard 85, which is coupled to a converter system 403, for converting digital signals from the computer 401 to analog signals to drive a heater controller 409 for controlling the heating of the extraction vessels during extraction, and to provide input signals to drivers 410, 411 and 412 which control the solenoids of the valve blocks, the gas valves, and the peristaltic pump 436, respectively. Converter 403 also serves as an analog to digital converter for providing signals to the computer 401 from spectrophotometer 335 and from conductivity meter 55, and from thermister 231 through 235. An example of such a converter 403 is a Hewlett-Packard 3497 interface. The computer also provides signals to a motor controller 405 for controlling a stepper motor used to oscillate the extraction vessels during mixing operations and to position the extraction vessels hoizontally for phase separation. A typical example of such a controller 405 is a Modulynx ™ Motion Control Interface Card, type 10d005A from Superior Electric.

SECOND PREFERRED EMBODIMENT

Figure 7:
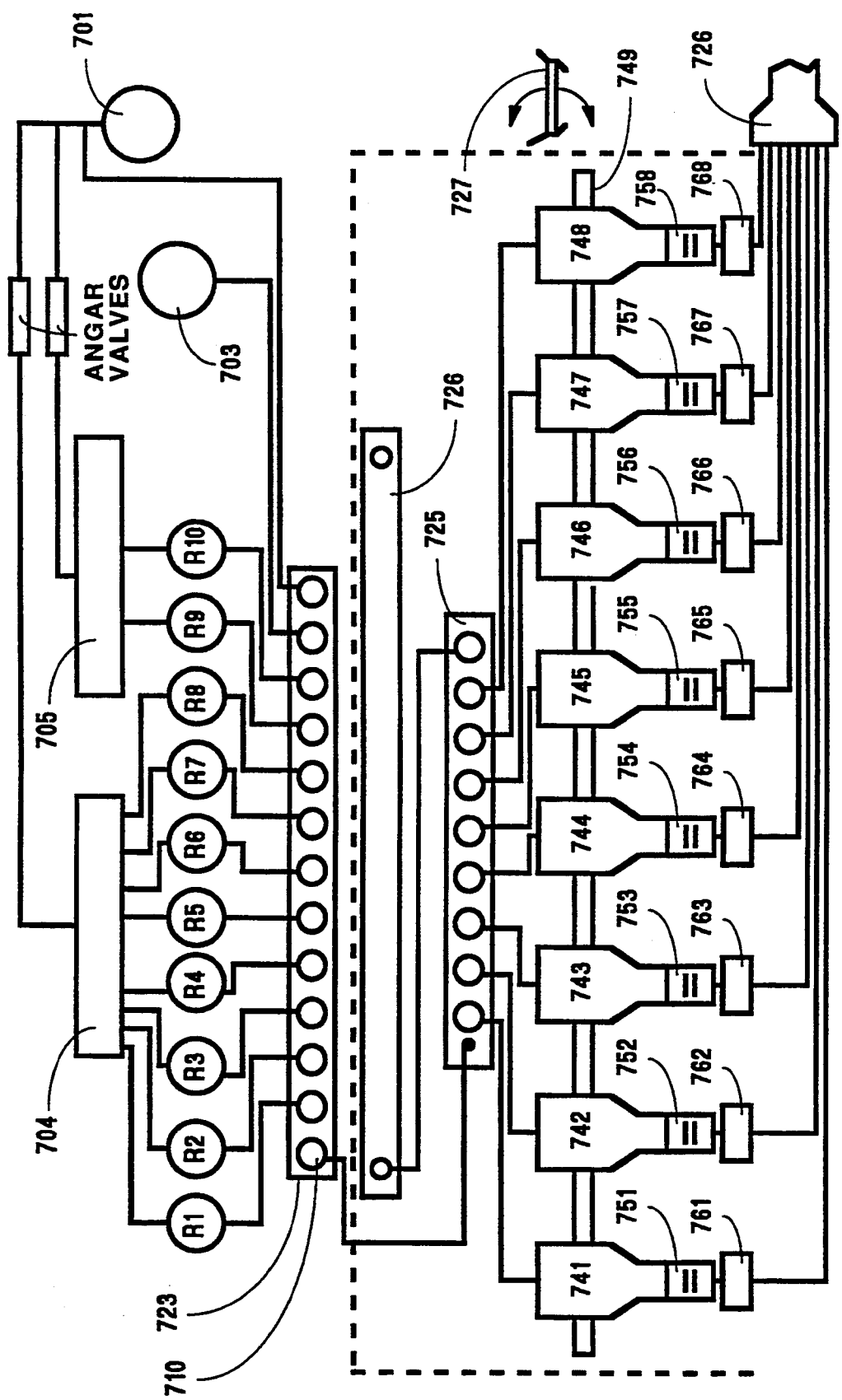
FIG. 7 shows a schematic representation of a second preferred embodiment of the invention.

Shown in FIG. 7 is a second preferred embodiment of the invention which provides for automatic extraction of nucleic acids but does not incorporate automatic dialysis. Rather, it is designed to mate with a dialysis cassette, hereinafter called a Dialysette ™ cartridge, so that after the extraction the dialysis can be performed independently if desired, for example at a reduced temperature. It is also adapted for use with methods of normal ethanol precipitation of nucleic acids.

This second embodiment includes a source of high pressure 701, typically about 10 psi guage, a source of low pressure 703, typically about 1.5 psi guage, a gas manifold 704 for the aqueous reagents, and a gas manifold 705 for the organic reagents. A typical selection of aqueous reagents is as follows: vessel R1 contains proteinase K; vessel R2 contains lysozyme; vessel R3 contains lysis buffer e.g. 4M urea, 0.2 NaCl, 100 mM Tris-HCl pH 8.0, 0.5% n-lauroyolsarcosine, 10 mM CDTA; vessel R4 contains 3M sodium acetate pH 5.5; vessel R5 is an extra vessel to be used as desired; vessel R6 contains 70% ethanol; and vessel R7 contains water. The organic reagents are as follows: vessel R8 contains ethanol; vessel R9 contains phenol/chloroform in a 50/50 ratio; and vessel R10 contains chloroform. An electrically operated valve block 723 is used to control the flow of reagents out of the various vessels R1–R10, with metering based on time and pressure as before. Port 710 in valve block 723 is connected to a valve block 725 which directs the flow of the various reagents to eight reaction vessels 741–748. A strip heater 749 is attached to each vessel to provide the desired temperature control during extraction. Valve block 725 and reaction vessels 741–748 are also coupled to a waste manifold 726. In this second embodiment, the reaction vessels 741–748, the waste manifold 726, strip heater 749, and the valve block 725 are all mounted on a rocker apparatus and are all rocked simultaneously about an axis 727 by a motor (not shown). As in the first embodiment, the oscillation about axis 727 during the extraction process is quite slow, about one per second, typically through an angle of 50° to 60°. Also, the apparatus is rocked so that the reaction vessels are in a full horizontal position during phase separation.

In this second embodiment, not only is the gas distribution simplified but so is the reaction vessel system. Instead of having to pressure transfer fluid out the top of each reaction vessel, the material in the reaction vessels can be removed by gravity flow since the vessels are of a flow through type, or it can be pressured out the bottom if so desired. Also at the bottom of reaction vessels 741–748 are conductivity cells 751–758, one for each vessel, for monitoring when the organic phase has been educted. Flow out of the reaction vessels is controlled by angar valves 761–768.

Figure 8:
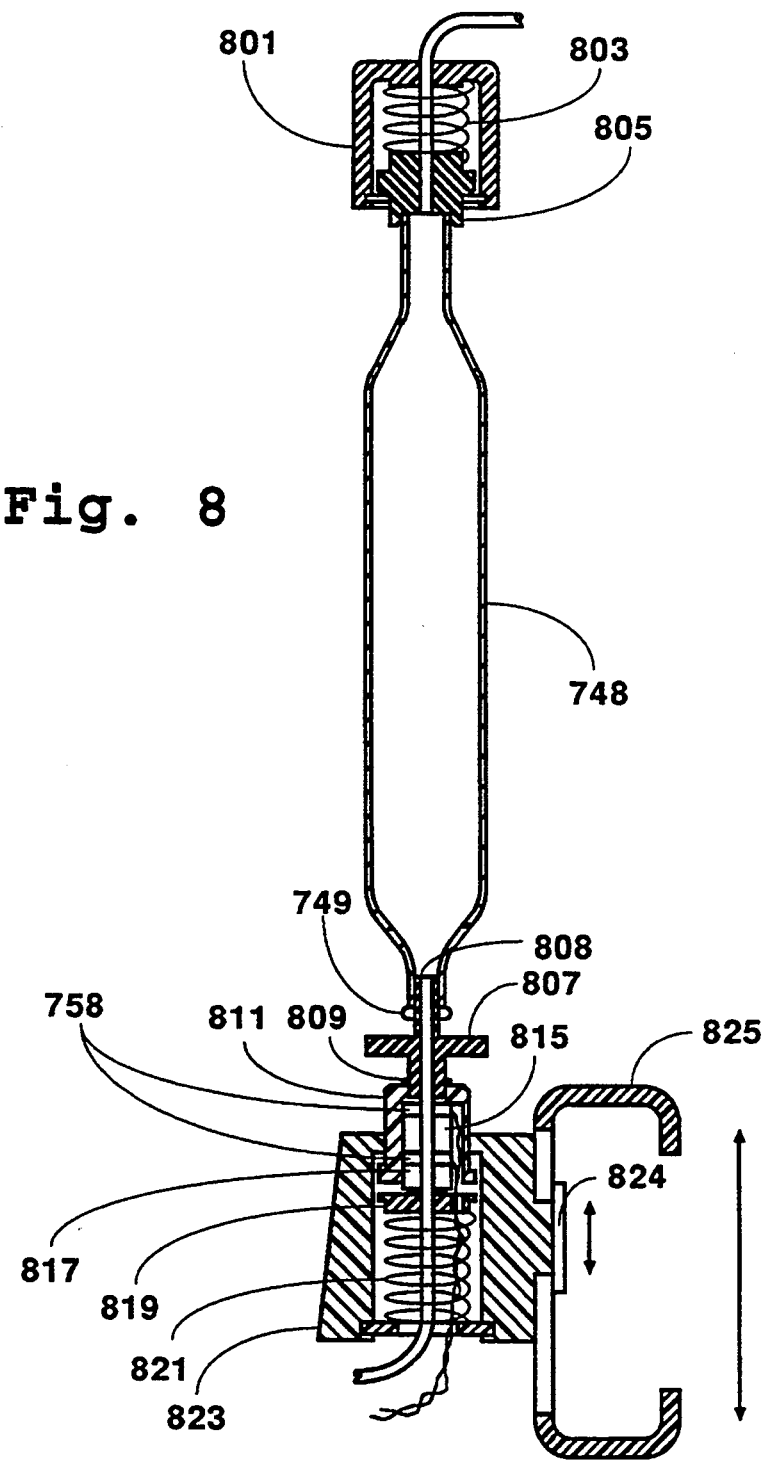
FIG. 8 shows a cross-sectional view of a reaction vessel according to the second embodiment of the invention and how it is sealed.

FIG. 8 shows a cutaway side view of a portion of the apparatus for holding the reaction vessels on the rocker apparatus. A cap 801 holds a springloaded seal 805 tightly against the top of reaction vessel 748. At the bottom, a run connector 807, typically polyethylene, seals the reaction vessel with a male Luer-type fitting 808. The run connector is removable to facilitate washing of the reaction vessel. In that instance, lip 749 of reaction vessel 748 rests against an O-ring 809, so that the entire interior of the reaction vessel can be cleaned and there is no dead space which can contribute to contamination.

A barrel 811 which moves inside a housing 823 holds run connector 807 in place. The conductivity cell 758 is typically gold coated for maximum sensitivity, i.e. to provide corrosion resistance. The two electrodes of the cell are separated by a teflon spacer 815. Another teflon spacer 817 holds the cell in place against a holding ring 819 which is loaded by a spring 821, thereby loading the entire assembly against the reaction vessel 748. Also, housing 823 is slideably attached to a mounting 825 via a pin 824 which slides up and down in mounting 825 to effect a tight seal of the run connector to the reaction vessel.

Figure 9:
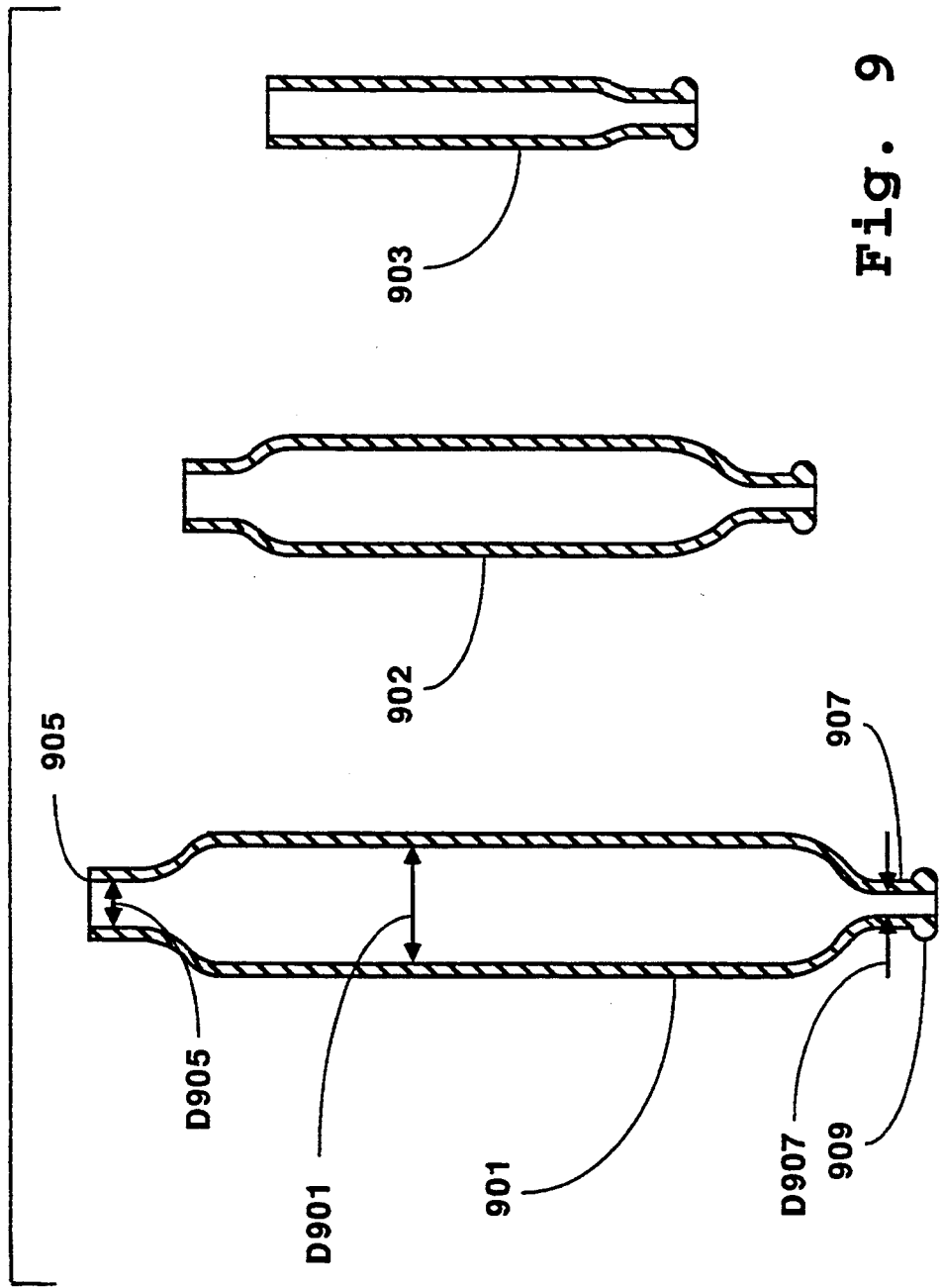
FIG. 9 shows three different shapes of reaction vessels according to the second embodiment of the invention.

Shown in FIG. 9 are three examples of reaction vessels designed for use in this second embodiment. Vessel 901 is a 14 ml vessel which is constructed of glass about 6 inches long and has a maximum internal diameter D901 of about 0.6 inches, an aspect ratio of about 10:1. Top 905 of the vessel 901 is cut square to seat firmly against springloaded seal 805, without providing any dead space to collect residual DNA. Since materials to be digested are introduced through top 905, the internal diameter D905 of the top is relatively large, about 0.25 inches. At the bottom of the vessel 901, the vessel necks down to an internal diameter D907 of about 0.156 inches and is ground internally to an angle of 1.7° to provide a female Luer-type fitting 907. At the very bottom of the vessel, a lip 909 is provided to effect a seal with O-ring 809 during cleaning. Reaction vessel 902 is a 7 ml vessel having an overall length of about 4.5 inches and a maximum internal diameter of 0.45 inches to provide an aspect ratio of about 10:1. Vessel 902 is provided with a female Leur-type fitting and a lip at the bottom as in vessel 901. Similarly the top is cut square and is the same size as that of vessel 901 to seat against seal 805. Reaction vessel 903 is a 3.5 ml vessel about 3.6 inches long and having a maximum internal diameter of about 0.36 inches, again an aspect ratio of about 10:1. The top and bottom of the vessel match those of vessels 901 and 902. The aspect ratio of 10:1 in each of these vessels is to provide a practical ratio for the cross-sectional area of a fluid in the vessels in the upright position to the area of a fluid in the vessel when it is in the horizontal position, thus, optimizing the step of phase separation. Even larger aspect ratios are desirable for phase separation, however, aspect ratios which are substantially larger than about 15:1 are not practical for other steps of the process, e.g. when mixing reagents in the vessel. Also, lower aspect ratios than 10:1 can be used, but lower than about 6.5:1 the phase separation is not significantly enhanced.

Figure 10:
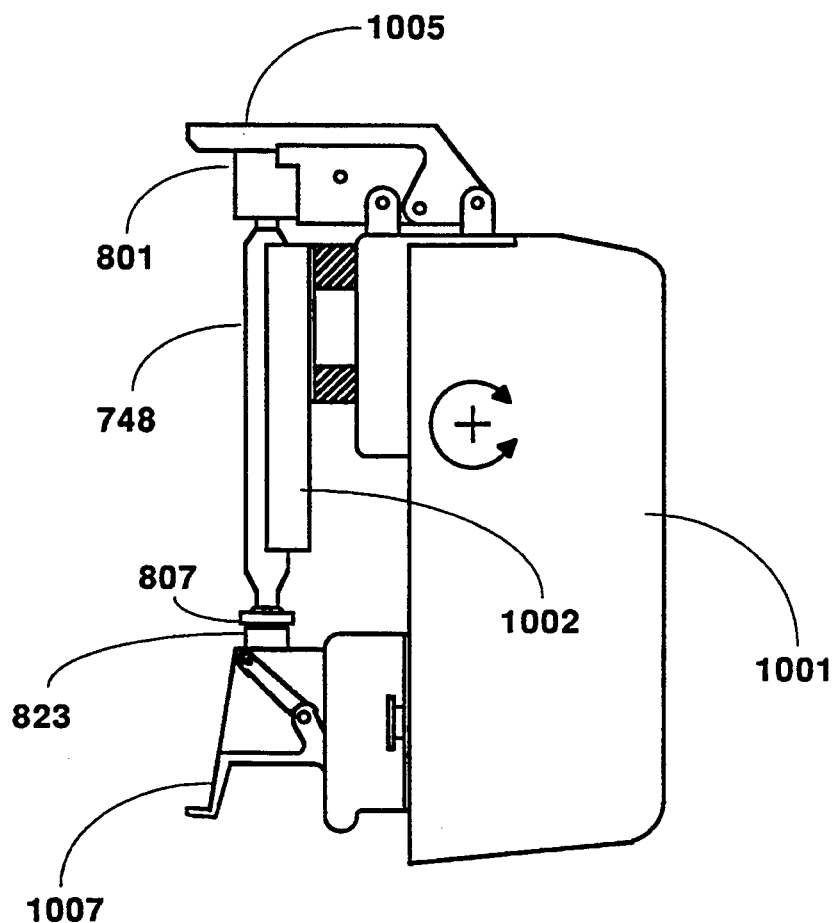
FIG. 10 shows a side view of a rocker apparatus according to the second embodiment.

FIG. 10 shows a side view of the rocker apparatus 1001 in its normal upright position. The rocker apparatus carries a cradle 1002 to which the reaction vessels are attached, typically by thermal epoxy. The cradle also holds the strip heater 749 in contact with the vessels. Mount 825 is slideably attached to rocker apparatus 1001 and holds the pin 824 (not shown) and housing 823 to permit the different length reaction vessels to be held in place. Cap 801 is held in place by a latch 1005 attached to rocker apparatus 1001 which clamps down on the cap and locks it into place to effect a tight seal between the springloaded seal 805 (not shown) and the reaction vessel 748. Run conector 807 is held firmly in place against the reaction vessel by a lever actuator 1007 which moves housing 823 up and down one side of mount 825 as described earlier.

Using this second embodiment to perform the extraction, the method of the invention must be slightly modified. First, the rocker apparatus 1001 is inverted, inverting the reaction vessels 741–748, and the vessels are vented to waste manifold 726, one at a time to avoid cross-contamination from vessel to vessel, and similarly for all further operations except a purge cycle, to be discussed later. Lysis buffer and proteinase K are then added via valve blocks 723 and 725 to the desired number of reaction vessels. The vessels are then preincubated at about 60° to remove any residual nuclease activity which may be present in the proteinase K for 5–10 minutes, while gently rocking the vessels. (To simplify the rest of the discussion, the process will be described relative to only one reaction vessel, vessel 748.) The rocker apparatus is then rocked back to its normal upright position and the cap 801 is removed by raising latch 1005. A nucleic acid sample is then added to the reaction vessel from the top and the latch 1005 is closed pressing cap 801 firmly onto the reaction vessel. The rocking apparatus is then moved to a nominal position 90° relative to its usual upright position, and the reaction vessel is rocked back and forth about the horizontal position while heating nominally to 60° to digest the sample. After digestion is complete, the rocker apparatus is turned upside down and the reaction vessel is vented to waste. The phenol/chloroform solvent is then delivered to the reaction vessel with the lysate via valve blocks 723 and 725 and the lysate and solvent are gently mixed by rocking back and forth about the horizontal position as in the first embodiment for about 15 minutes to extract the contaminating protein from the nucleic acids. Once the extraction is complete, the rocker apparatus is stopped and the reaction vessel is held in a horizontal position for about 5 minutes while the vessel is heated to bring about the phase separation. Once phase separation has occurred, the rocker apparatus 1001 is rocked to a position so that the bottom of the reaction vessel is about 10° above the horizontal and the Anger valve 768 is vented to waste manifold 726 to relieve the pressure built up by heating. The Angar valve 768 is then closed and the vessel is moved to the upright position and the lower phenol phase is educted to waste manifold 726. The conductivity cell 758 is used to detect the change in phase in order to stop educting material from the reaction vessel. The above extraction process is then repeated as before until the upper phase is protein free. The time for these subsequent extraction typically remain about 10–15 minutes. However, the subsequent phase separation typically occurs in shorter times, 2–3 minutes.

Once the above extraction procedure is complete, either of two methods of concentrating the nucleic acids is available, dialysis or ethanol precipitation.

Figure 11A:
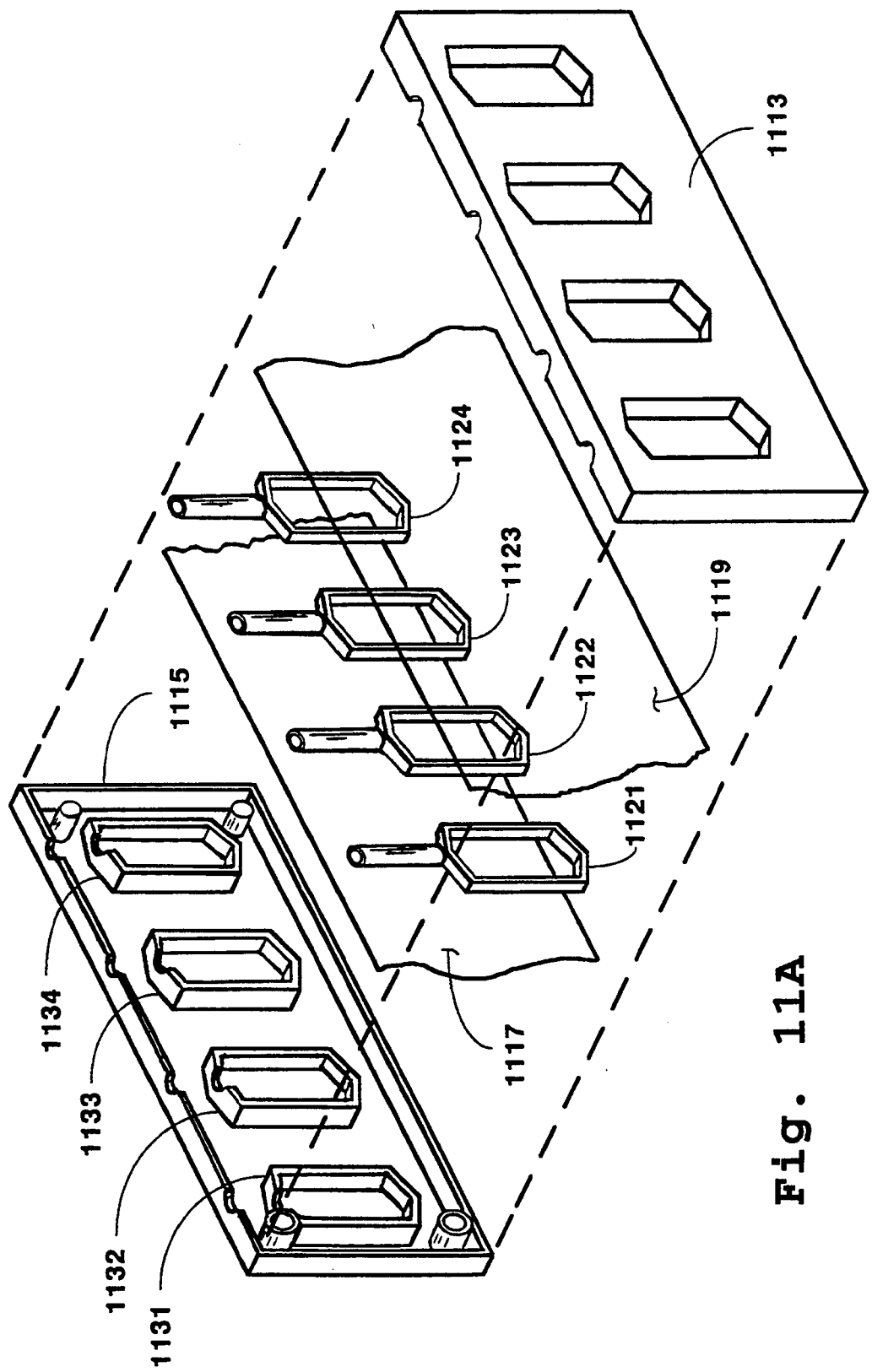
FIG. 11A shows an expanded view of a dialysis cartridge used with the second embodiment.

Shown in FIG. 11A is a construction drawing of a Dialysette TM cartridge 1100 especially designed to fit onto the female Luer-type fittings at the bottom of the reaction vessels. The cartridge is made up of two frame halves 1113 and 1115 between which are sandwiched two dialysis membranes 1117 and 1119 and a set of gaskets 1121, 1122, 1123, and 1124, the gaskets being sandwiched between the dialysis membranes. Each of the frame halves has a series of raised windows 1131–1134 which, when the frame halves are fastened together, clamp the dialysis membranes and gaskets firmly in place providing four reservoirs defined by the space between the membranes which is provided by gaskets 1121–1124.

Figure 11B:
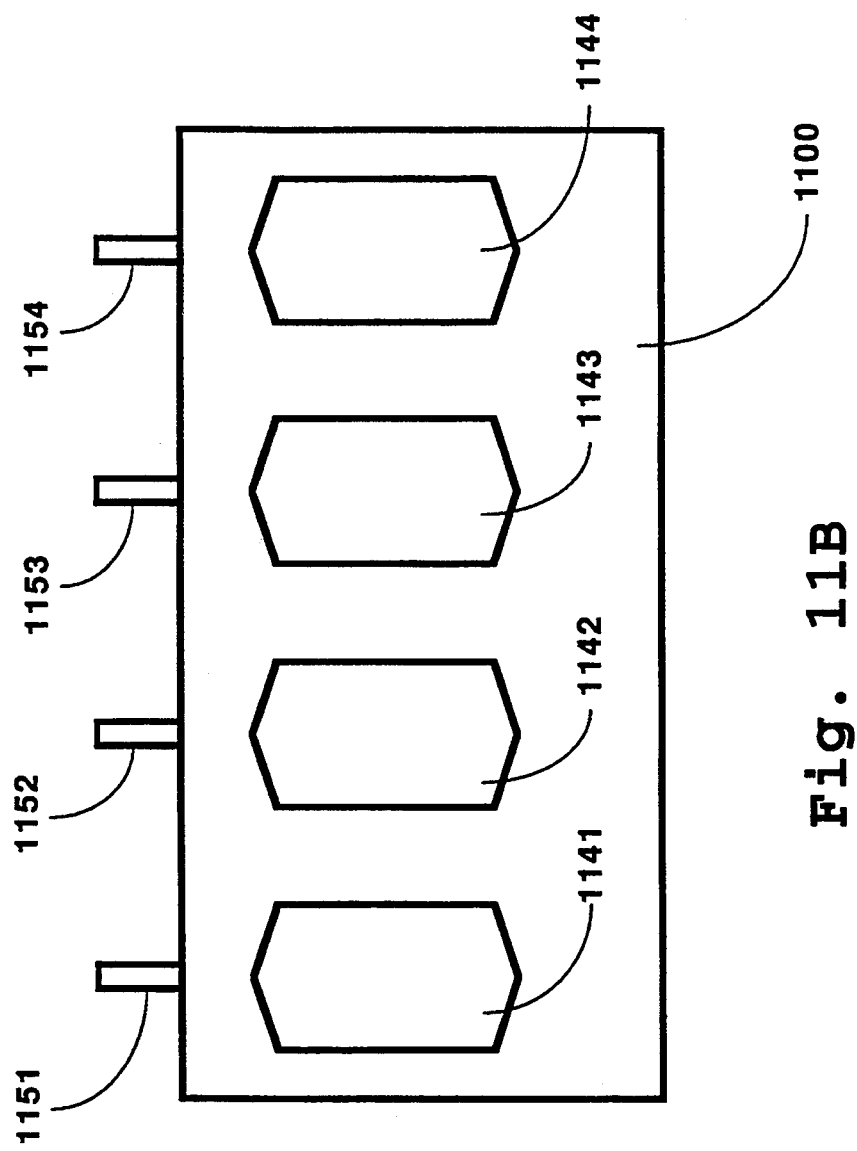
FIG. 11B shwos the completed cartridge of FIG. 11A.

FIG. 11B shows a completed structure with the four reservoirs 1141–1144. To fill the reservoirs, the gaskets are provided with a fill tube which have male Luer-type fittings 1151–1154 at the top. Also, each of the fill tubes is spaced apart precisely the same distance that the reaction vessels are spaced apart in order to fit therein.

Figure 12C:
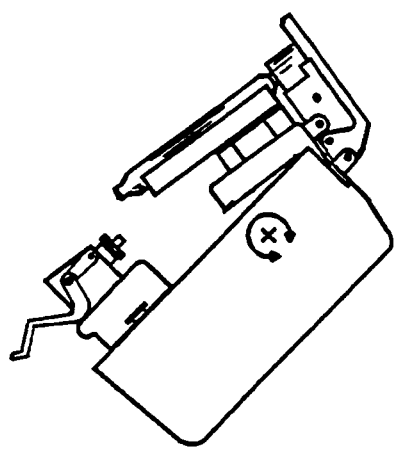
FIGS. 12A–12F shows a method used to fill the dialysis cartridge of FIG. 11B.
Figure 12F:
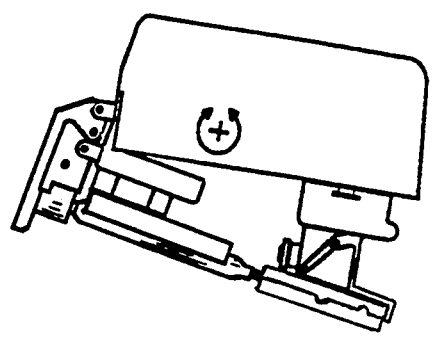
Figure 12B:
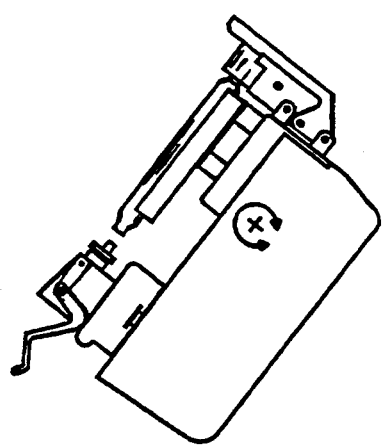
Figure 12E:
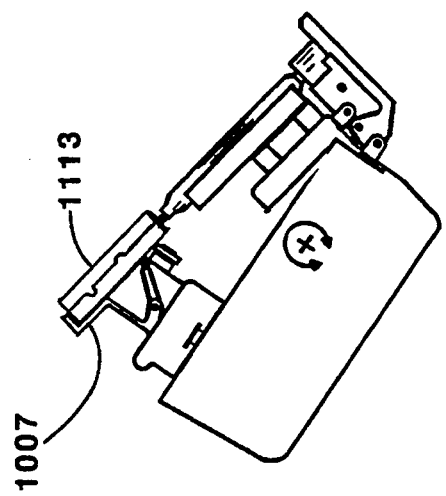
Figure 12A:
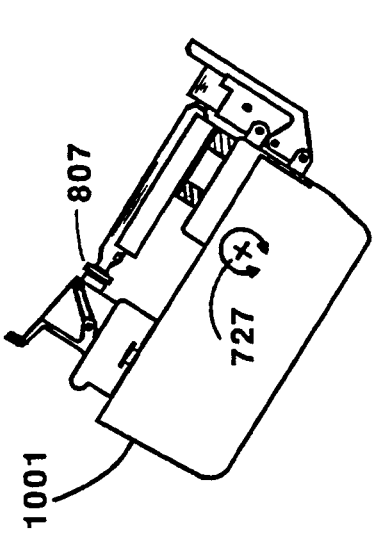
Figure 12D:
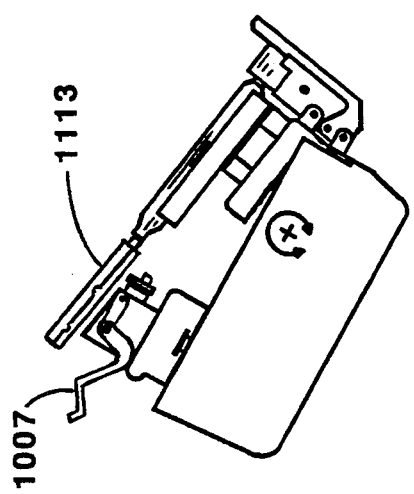

FIGS. 12A–12B illustrate the method used to attach and fill the dialysette cartridges. First, the Dialysette cartridge rocked to a simi-upright position as shown in FIG. 12A. The reaction vessels are then opened, as illustrated in FIG. 12B, and the vessels are swung away from the rocker apparatus 1001 somewhat, as illustrated in FIG. 12C, in order to attach the cartridge. The Dialysette cartridge 1113 is then attached as in FIG. 12D, and clamped into place as in FIG. 12E with lever actuator 1007, and the other corresponding lever actuators which are used for the other reaction vessels. The rocker apparatus is then rocked back to the position illustrated in FIG. 12F, thereby filling the reservoirs in the Dialysette cartridge.

Figure 13:
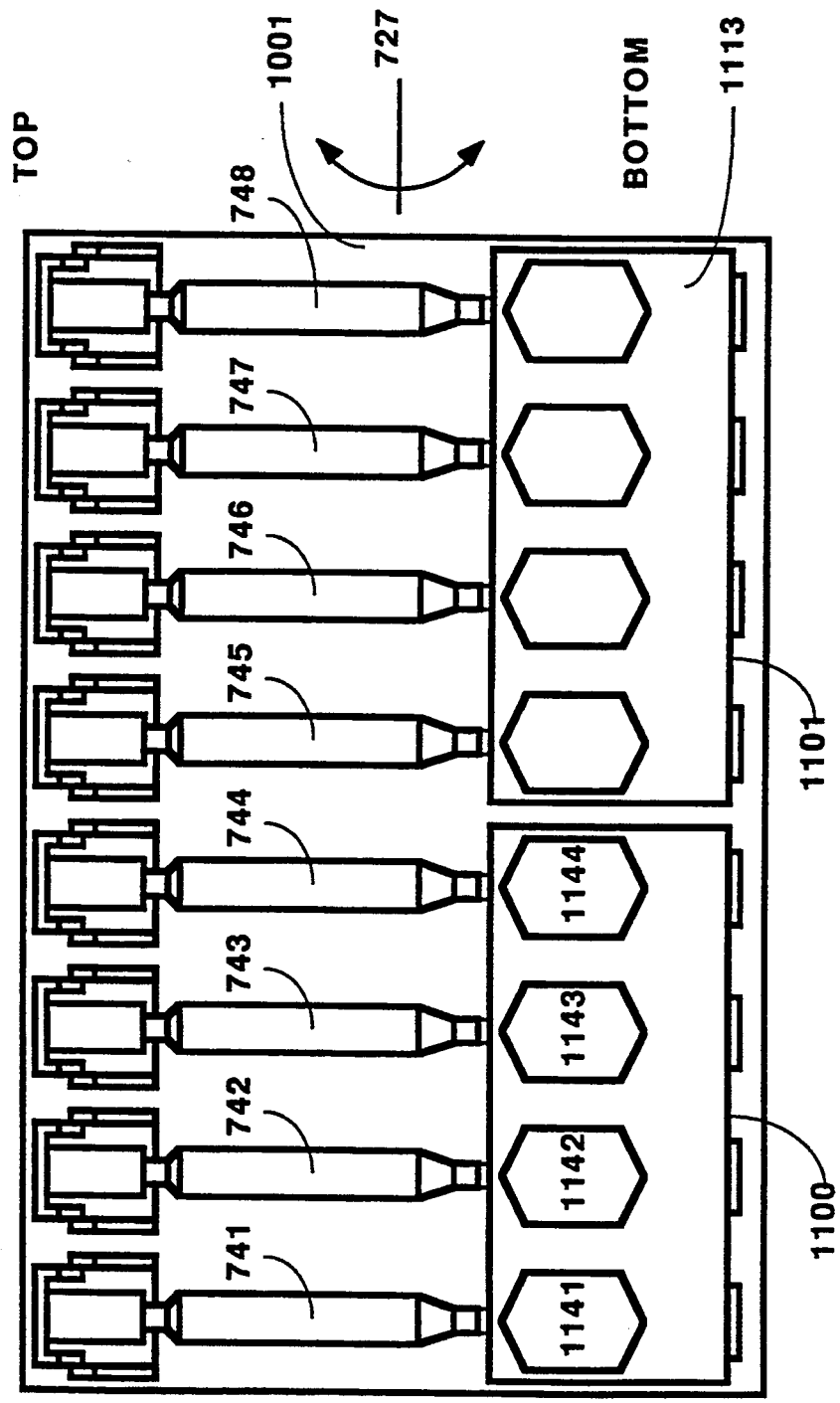
FIG. 13 shows a front view of dialysis cartridges attached to the rocker apparatus of the second embodiment.

FIG. 13 shows a front view of the rocker apparatus with dialysette cartridges 1100 and 1101 attached to the reaction vessels 741–748. Once the Dialysette cartridges are filled, they are removed and plugged and standard dialysis procedures are used to concentrate and purify the extracted nucleic acids. For a detailed description of the Dialysette cartridge see copending application entitled "Dialysette TM Dialysis Cartridge" filed Apr. 10, 1986 by G. Richard Cathcart, et al.

The other approach to concentrate the nucleic acids, i.e. ethanol precipitation, is also enhanced by the structure of the apparatus. To concentrate the nucleic acids in vessel 748 by standard ethanol precipitation, a volume of sodium acetate is added to the reaction vessel from reagent vessel R4 which is equal to 0.1 the volume of the remaining lysate. Then two volumes of punctilious ethanol from reagent vessel R8 is added and the vessel is gently rocked to precipitate nucleic acids. The two volumes of ethanol correspond to twice the volume of the lysate and sodium acetate together.

Figure 14:
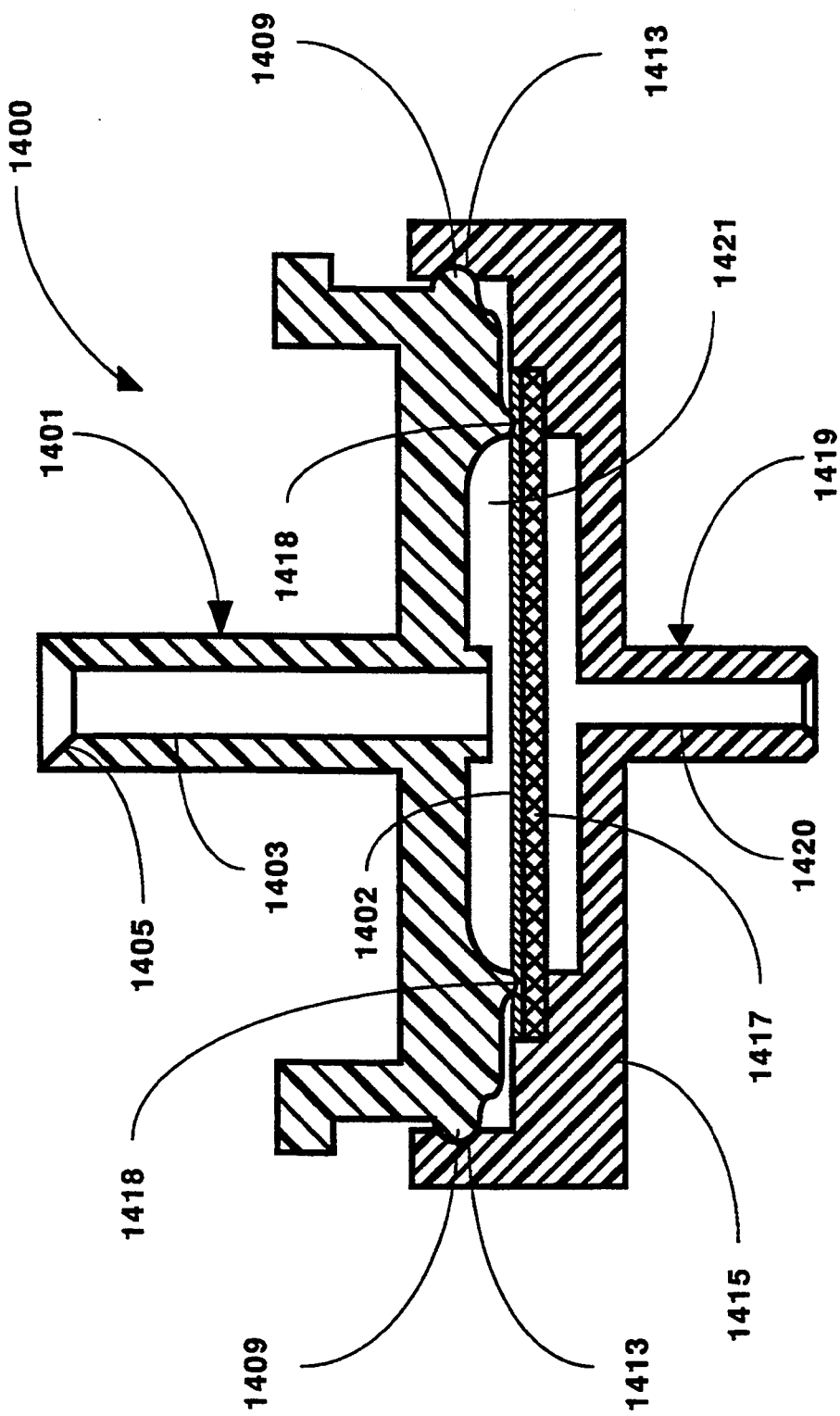
FIG. 14 shows a precipitate collection unit used with the second embodiment.

To collect the precipitated nucleic acids, a special collection device known hereinafter as a Precipitette TM collection unit 1400 is used. FIG. 14 shows a cross-section of the collection unit 1400. The unit is made up of a circular top portion 1401 which has an upward extending element that at the very top has the form of a male Luer-type fitting to fit into the bottom of a reaction vessel. A circular tube 1403 runs through top portion 1401 and has a smooth chamfered surface 1405 in order to inhibit the collection of nucleic acids on the surface of the unit. The top portion 1401 has a snapping ring 1409 which snaps into circular detent 1413 located in a bottom portion 1415 in order to hold the top portion 1401 and bottom portion 1415 together. Sandwiched between the top and bottom portions is a support mesh 1417 for holding a filter 1402 thereon. A circular protrusion 1418 presses the filter 1402 against the mesh 1417 and holds both filter and mesh in place in the unit. A bottom portion 1419 is provided which fits directly into barrel 811 where the run connector 807 is normally attached. Also, bottom portion 1419 is provided with a tube 1420 in order to connect the unit to waste. A volume 1421 between the bottom of top portion 1401 and the mesh is provided to collect the precipitated nucleic acids.

To use the Precipitette TM collection unit 1400, once the ethanol precipitation has been performed, the rocker apparatus is rocked to its upside down position. The run connectors are removed and the Precipitette collection units are installed in their places. The rocker unit is then vigorously rocked to its normal upright position while at the same time during this down stroke pulsing in air and ethanol to flush the precipitates from the sides of the reaction vessels and into the Precipitette collection units. The pulsing of the air and ethanol is performed in alternate cycles, the air typically for about 600 msec. at a time and the ethanol for about 300 msec. at a time although these times can vary depending on the size of the reaction vessel being cleared. As the precipitate is flushed from the reaction vessels, it is collected in filters 1402 in the collection units. If desired, the precipitates can be further washed by filling the reaction vessels with ethanol and draining them to waste through the collection units. The precipitate can then be collected by removing the filters from the collection units.

Following either dialysis or precipitation, the reaction vessels must be scrupulously cleaned before they can be reused, since a piece of left over DNA could get replicated over and over in future experiments. To accomplish this cleaning, a purge cycle is instituted where each vessel is purged independently to avoid cross-contamination. This sequence is as follows. First, each vessel is rinsed by adding water which is heated in the vessel to about 60° C. Each vessel is rocked vigorously and, the hot water is blown to waste, one at a time. Then 6 normal nitric acid is added to each vessel and heated to about 60° C. while rocking vigorously. Then the nitric acid is blown to waste one vessel at a time. Each vessel is then rinsed with water, heated to 60° C., rocked vigorously, and then the water is blown to waste again one at a time. A 50/50 mixture of Lysis buffer and water is added to each vessel to neutralize the nitric acid, heated to 60° C., and the vessels rocked and blown to waste as before. Then each vessel is rinsed twice with water just as in the first water rinse. Each of the above cycles requires approximately three minutes. Following the purge operation, the reaction vessels are again ready for use.

Computer control of this second embodiment is substantially similar to that of the first embodiment except simpler since there are fewer valves to operate, no dialysis pumping system, and no spectrophotometer to monitor.

COMPUTER SOFTWARE SYSTEM

At the most basic level, software control of the extraction apparatus is a matter of opening and closing valves and turning switches on and off at the proper times to achieve the desired flows of the various materials from one vessel to another and to perform the required operations. The fact that the method of the invention is a sequence of steps lends itself conveniently to software control. The following is an example of a specific instruction set used for the first preferred embodiment for each step of the extraction method which can be easily translated into whatever programming language it is desired to use. It is based on the assumption that reagent vessel 1 contains the lysis buffer, reagent vessel 2 contains the proteinase K, reagent vessel 3 contains the phenol/chloroform/isoamyl alcohol, reagent vessel 4 contains chloroform, and reagent vessel 5 contains RNase.

| Command Number | Command |
|---|---|
| STEP 1: TISSUE DIGESTION | |
| 10 | Open valves 22; 50 (port 91); 51 (port 80, 81); 61. |
| | Close all valves 4 minutes after command 10. |
| Comment: | Delivery of lysis buffer to vessel 1 is now complete. |
| 30 | Open valves 24; 50 (port) 92; 51 (ports 80, 81); 61. |
| 40 | Close all valves 0.5 minutes after command 30. |
| Comment: | Delivery of proteinase K is now complete. |
| 50 | Turn on heater, 221 of vessel 1; raise temperature to 55° C. and maintain. |
| 60 | Turn on motor 201; angle of rotation set for ±60° with period of 1 second. |
| 70 | Turn off motor 201; and heater 221 3 hours after command 60. |
| 80 | Wait for cooling of digested mixture. |

| Command Number | Command |
|---|---|
| STEP 2: EXTRACTION | |
| 90 | Open valves 26; 50 (port 93); 51 (ports 80, 81); 61. |
| 100 | Close all valves except valve 61, 5 minutes after command 90. |
| Comment: | Delivery of the extraction mixture (phenol/chloroform/isoamyl alcohol is now complete. |
| 110 | Turn on motor 201; angle of rotation set for ±60°; period 1 second. |
| 120 | Turn off motor 201, 20 minutes after command 110. |
| STEP 3: SEPARATE PHASES | |
| 140 | Turn on motor 201, angle of rotation set for, 90°. |
| 150 | Turn off motor, 201 when angle of rotation reaches 90°. |
| Comment: | Extraction vessel is now being held in a horizontal position. |
| 160 | Turn on thermister 231; increase temperature to 550° C. and maintain. |
| 170 | Turn off thermister 231 12 minutes after temperature reaches 55° C. under command 150. |
| STEP 4: RETURN EXTRACTION VESSEL TO UPRIGHT POSITION | |
| 180 | Turn on motor 201, 12 minutes after temperature reaches 55° C.; angle of rotation set for 0°; descent rate set for 9°/second. |
| STEP 5: WITHDRAW PHENOL PHASE | |
| 190 | Close valve 61. |
| 200 | Open valves 62; 51 (port 81); 52 (ports 71, 72). |
| 210 | Monitor conductivity with conductivity meter 55. |
| 220 | 1.0 seconds after conductivity reaches $10^4$ Mhos, close all valves. |
| Comment: | The one second delay in command 220 after the conductivity goes high is to ensure that residual phenol left in the delivery lines to value block 52 has been removed. |
| 230 | Open valves 52 (port 74); 61. |
| 240 | Close all valves 30 seconds after command 230. |
| 250 | Open valves 52 (ports 71, 73); 39; 51 (port 81); 61. |
| Comment: | Command 250 backflushes valve block 52 and forces aqueous solution left in the delivery lines back into extraction vessel 11 for further extraction or purification. |
| STEP 6: REPEAT EXTRACTION PROCESS | |
| 270 | Perform commands 90 through 250, N times. |
| Comment: | N, the number of extractions performed, is chosen by the programmer based on experience and on the type of sample tissue. |
| 280 | Open valves 28; 50 (port 94); 51 (port 80, 81); 61. |
| Comment: | Command 280 adds chloroform to extraction vessel 11 for the final extractions. |
| 290 | Close all valves except valve 61. |
| 300 | Repeat steps 110 through 261 |

-continued

| Command Number | Command |
|---|---|
| | one time. |
| STEP 7: REMOVE AQUEOUS SOLUTION (To Dialysis) | |
| 310 | Open valves 51, (port 81, 82); 62; 321. |
| 320 | Close all valves 5 minutes after command 310 |
| Comment: | The aqueous solution in extraction vessel 11 is now dialysis bag 411. |
| STEP 8: DIALYZE AQUEOUS SOLUTION | |
| 330 | Turn on pump 337. |
| 340 | Open valve 324. |
| 350 | Monitor A270 with spectrophotometer 335. |
| 360 | When A270 is less than or equal to 0.01, close all valves and turn off pump 337. |
| STEP 9: REMOVE RNA FROM AQUEOUS SOLUTION (optional) | |
| 370 | Open valve 324; open valve 51 (ports 81, 82); 61. |
| 380 | Close all valves 5 minutes after command 370. |
| Comment: | The dialyzed aqueous solution in dialysis bag 311 is in extraction vessel 11. |
| 390 | Open valves 30; 50 (port 95); 51 (ports 80, 81); 61. |
| 400 | Repeat Steps 90 through 360. |
| STEP 10: COLLECT SAMPLE | |
| 410 | Open valves 324; 51 (port 95); 51 (ports 71, 75). |
| 420 | Close all valves 5 minutes after command 410. |

UTILITY OF THE INVENTION

Examples: Preparation of DNA from Human Lymphocytes

Lymphocytes are first washed from one unit of whole blood and are resuspended in 4 ml balanced salt solution. (Balanced salt solution is made up of 1 volume of solution A and 9 volumes of a solution B, where solution A is 0.1% glucose, $5 \times 10^{-10}$M $CaCl_2$, $9.8 \times 10^{-4}$M $MgCl_2$, $5.4 \times 10^{-3}$, KCl, 0.145M Tris-HCl, pH 7.6; and Solution B is 0.14M NaCl.) Then 0.35 ml of the lymphocyte suspension above is mixed with 4 ml lysis buffer (1M NaCl, 1% SDS, 8M urea, 10 mM EDTA, 50 mM Tris-HCl, pH 8.0), and 1 mg of proteinase K in 0.65 ml lysis buffer to obtain a total volume of 5 ml. The digestion is performed in a conical tube (extraction vessel 11) as described earlier, at 55° C. for 3 hours. About 5 ml of phenol/chloroform/isoamyl alcohol 50:48:2 is added to the tube and the two phases are mixed according to the protocol for 20 minutes. The extraction vessel is then rotated to the horizontal position for 10 minutes at 55° C. to allow the phases to separate. The extraction vessel is then rotated slowly back up to the vertical position over a period of about 10 seconds, and the lower organic layer is removed to waste. A second extraction is performed with the phenol/chloroform/isoamyl alcohol mixture and a third extraction is performed using 5 ml of chloroform. The chloroform is removed to waste and the aqueous DNA-containing layer is pressure transferred to a dialysis bag, such as dialysis bag 311. This aqueous solution is then pressure dialyzed according to the protocol until A270 is below 0.01. The final DNA solution is then educted from the bag and collected.

Following this process yields about 1 ml of DNA solution containing about 250 micrograms of DNA. The resulting solution has an absorbance ratio A230:A260 of 0.52 and an absorbance ratio A260:A280 of 1.90, demonstrating very high purity. (For absolutely pure DNA, the absorbance ratio A230:A260 is $0.5 \pm 0.05$ and A260:A280 is $1.9 \pm 0.1$.) Analysis of the sample using a 0.8% agarose gel and standard ethidium bormide staining techniques shows a single band with a size greater then 50 kbase pairs (i.e., greater than $3.5 \times 10^7$ daltons). Also most importantly, digestion with the enzyme Eco RI is positive, indicating that the DNA is pure and therefore restrictable, a very stringent test for DNA purity.

Variations on the above example demonstrate the importance of heating and increasing the surface area to effect the phase separation step. For example, for human lymphocytes, if the extraction vessel is not heated, but is maintained at room temperature, and the extraction vessel is not rotated to a horizontal position, phase separation typically requires over 60 minutes. If instead the extraction vessel is heated to 55° C. but is not also rotated to the horizontal position, the phase separation requires over 4 minutes. With heating to 55° C. and rotation of the extraction vessel to the horizontal position, the phase separation typically requires only about 2.5 minutes. In each of these variations, however, the high salt content is enhancing the rate of phase separation by approximately a factor of two.

While there has been shown and described a preferred embodiment of the apparatus and method of the present invention, it will be apparent to those skilled in the art that many changes and modifications may be made without departing from the invention in its broader aspects. For example, it is apparent that the extraction vessel need not be rotated to a horizontal position to speed up phase separation, although it does have a major influence. Similarly, the phase separation can be performed at a temperature below the preferred range of 45° C. to 55° C., but it will proceed at a slower rate, and the further below that range the slower the rate. In terms of apparatus it will be apparent that automated devices according to the invention can be constructed with either more or fewer extraction vessels, reagent vessels, and dialysis bags. Also, some valves may be conveniently placed at different locations in the apparatus, for example valve block 52 may be placed ahead of conductivity meter 55. However, this would result in some loss of the aqueous phase when the flow is stopped. In addition, the specific model numbers chosen for the various pieces of apparatus included in the automated extraction system are not meant to be restrictive as to the particular models which can be used, but are offered by way of example only. Also, it will be apparent that the apparatus may be only partially automated, by providing the fluid delivery system 100 and chamber/rocker system 200 independent of the dialysis system 300.

We claim:

1. A method of extracting nucleic acids from cells comprising the steps:
   (a) creating a lysate by treating said cells with proteinase K in the presence of a lysis buffer;
   (b) mixing said lysate with a phenol-based solvent system, thereby creating an emulsion;
   (c) heating said emulsion to a temperature greater than 35 degrees C. in the absence of mixing action and without centrifugation to promote separation of said emulsion into an aqueous phase containing said nucleic acids and an organic phase containing phenol and denatured proteins;

(d) removing said organic phase to leave a remaining aqueous phase containing said nucleic acids.

2. The method of claim 1 wherein the temperature in Step (c) is greater than 45 degrees C.

3. The method of claim 1 wherein the temperature in Step (c) is about 55 degrees C.

4. The method of claim 1 wherein Steps (b), (c), and (d) are repeated, in order, N times, where N is a number greater than or equal to 1.

5. The method of claim 4 wherein after Steps (b), (c), and (d) have been repeated N times, the remaining aqueous phase is mixed with chloroform sufficiently to create an emulsion and Steps (c) and (d) are repeated to leave an aqueous phase containing said nucleic acids.

6. The method of claim 5 wherein the remaining aqueous phase after mixing with chloroform is dialyzed.

7. The method of claim 5 wherein said lysis buffer comprises a detergent and a high concentration of a salt.

8. The method of claim 7 wherein said lysis buffer further comprises a chaotropic agent.

9. The method of claim 8 wherein said lysis buffer comprises a chelating agent.

10. The method of claim 9 wherein said lysis buffer further comprises a buffer.

11. The method of claim 10 wherein said lysis buffer comprises urea, NaCl having a molar concentration between 0.5 and 2, a detergent Tris-HCl, and EDTA.

12. The method of claim 6 wherein the temperature of Step (c) is about 55 degrees C.

13. The method of claim 6 wherein said phenol-based solvent system comprises a mixture of phenol, chloroform, and an antisurfactant.

14. The method of claim 13 wherein the antisurfactant is isoamyl and the ratios of phenol to chloroform to isoamyl alcohol are about 50:48:2.

15. The method of claim 6 wherein the lysis buffer comprises 8M urea, 1M NaCl, 1% SDS, 50 mM Tris-HCl, and 10 mM EDTA, pH 8.0.

16. The method of claim 1 further comprising the step: (e) increasing the surface area of the emulsion thereby further promoting phase separation, Step (e) occuring after Step (c) but before Step (d).

17. The method of claim 16 wherein Steps (b), (c), (e), and (d) are repeated N times in that order, where N is a number greater than or equal to 1.

18. The method of claim 16 wherein after Steps (b), (c), (e), and (d) have been repeated N times, the remaining aqueous phase is mixed with chloroform thereby creating an emulsion, and Steps (c), (e), and (d) are repeated in that order to leave an aqueous phase containing said nucleic acids.

19. The method of claim 16 wherein the remaining aqueous phase after mixing with chloroform is dialyzed.

* * * * *